(12) United States Patent
Yen et al.

(10) Patent No.: US 9,793,490 B2
(45) Date of Patent: Oct. 17, 2017

(54) ORGANIC OPTOELECTRONIC MATERIAL AND USE THEREOF

(71) Applicants: Feng-Wen Yen, Taipei (TW); Chin-Min Teng, Miao-Li (TW)

(72) Inventors: Feng-Wen Yen, Taipei (TW); Chin-Min Teng, Miao-Li (TW)

(*) Notice: Subject to any disclaimer, the term of this patent is extended or adjusted under 35 U.S.C. 154(b) by 0 days.

(21) Appl. No.: 15/011,647

(22) Filed: Jan. 31, 2016

(65) Prior Publication Data

US 2016/0233427 A1 Aug. 11, 2016

Related U.S. Application Data

(60) Provisional application No. 62/114,593, filed on Feb. 11, 2015.

(51) Int. Cl.
| | |
|---|---|
| *H01L 51/00* | (2006.01) |
| *C07D 487/14* | (2006.01) |
| *C07D 495/14* | (2006.01) |
| *C07D 333/76* | (2006.01) |
| *C07D 251/34* | (2006.01) |
| *C07D 239/26* | (2006.01) |
| *C07C 13/62* | (2006.01) |
| *C09K 11/02* | (2006.01) |
| *C09K 11/06* | (2006.01) |
| *C07D 251/24* | (2006.01) |
| *C07D 519/00* | (2006.01) |
| *C09B 57/00* | (2006.01) |
| *H01L 51/50* | (2006.01) |
| *H01L 51/42* | (2006.01) |
| *H01L 51/05* | (2006.01) |

(52) U.S. Cl.
CPC .......... *H01L 51/0056* (2013.01); *C07C 13/62* (2013.01); *C07D 239/26* (2013.01); *C07D 251/24* (2013.01); *C07D 333/76* (2013.01); *C07D 487/14* (2013.01); *C07D 495/14* (2013.01); *C07D 519/00* (2013.01); *C09B 57/00* (2013.01); *C09K 11/02* (2013.01); *C09K 11/06* (2013.01); *H01L 51/0072* (2013.01); *H01L 51/0074* (2013.01); *C07C 2603/54* (2017.05); *C09K 2211/1011* (2013.01); *C09K 2211/1059* (2013.01); *C09K 2211/1074* (2013.01); *C09K 2211/1092* (2013.01); *H01L 51/0558* (2013.01); *H01L 51/424* (2013.01); *H01L 51/5076* (2013.01); *H01L 51/5096* (2013.01); *Y02E 10/549* (2013.01)

(58) Field of Classification Search
None
See application file for complete search history.

(56) References Cited

FOREIGN PATENT DOCUMENTS

WO 2012141273 10/2012

OTHER PUBLICATIONS

Garcia-Frutos et al, Journal of Materials Chemistry (2011), 21(19), pp. 6831-6836.*
Journal of Materials Chemistry A, 2013,1,4077. Jang Hyuk Kwon et al,. Title : New interfacial materials for rapid hole-extraction in organic photovoltaic cells.

* cited by examiner

*Primary Examiner* — Zinna Northington-Davis

(57) ABSTRACT

The present invention generally discloses an organic optoelectronic material and organic electroluminescent (herein referred to as organic EL) device, organic photovoltaics (herein referred to as OPV) device and organic thin-film transistor (herein referred to as OTFT) device using the organic optoelectronic material. More specifically, the present invention relates to the organic optoelectronic material formula (1), and an organic EL device, OPV device and OTFT device employing the organic optoelectronic material can improve performance.

3 Claims, 3 Drawing Sheets

ORGANIC OPTOELECTRONIC MATERIAL AND USE THEREOF

This application claims benefit of provisional of U.S. Patent Ser. No. 62/114,593, filed Feb. 11, 2015.

FIELD OF INVENTION

The present invention generally relates to an organic optoelectronic material and organic electroluminescent (herein referred to as organic EL) device, organic photovoltaics (herein referred to as OPV) device and organic thin-film transistor (herein referred to as OTFT) device using the organic optoelectronic material. More specifically, the present invention relates to the organic optoelectronic material having general formula (1), an organic EL device, OPV device or OTFT device employing the organic optoelectronic material can improve performance.

BACKGROUND OF THE INVENTION

Organic optoelectronic material has been developed for several decades. Recently the organic optoelectronic material are widely put in use in organic optoelectronic devices, such as organic EL device, OPV device and OTFT device have attracted significant attention for industries practice use due to their potential application for flat-panel and flexible display, solid-state lighting, solar energy storage, etc. Organic EL is a light-emitting diode (LED) in which the emissive layer is a film made by organic compounds which emits light in response to an electric current. The emissive layer of organic compound is sandwiched between two electrodes. Organic EL device have many advantages such as self-emitting, wider viewing angles, faster response speeds and highly luminescence. Their simpler fabrication and capable of giving clear display comparable with LCD, making organic EL device an industry display of choice and has stepped into commercialization. An organic photovoltaic (OPV) device includes a substrate, a first electrode, a second electrode and a photoelectric conversion layer. The first electrode is disposed on the substrate. The second electrode is disposed on the first electrode. The photoelectric conversion layer is disposed between the first electrode and the second electrode. The device cell has electrical charge generated by absorbing the light. OPV has been considered as a highly growing trend for green energy technology because of its low cost, simple preparation and large area capability. The conversion efficiency of OPV had reached to the practical application. An organic thin-film transistor (OTFT) including, on a substrate having an insulating surface, at least a gate electrode, a gate insulating film formed in contact with the gate electrode, an organic semiconductor film formed in contact with the gate insulating film, and at least a pair of source-drain electrodes formed in contact with the organic semiconductor film, a carrier generating electrode to which carriers can be injected in response to a gate signal is implanted within the organic semiconductor film. OTFT has grown into a hotspot in organic electronics as it also possesses the merits of low cost, flexibility, low temperature processing and large area capability. And its performance is already comparable to that of the amorphous silicon based thin film transistors.

However, there are still many technical problems remaining to be solved in organic optoelectronic devices, such as material instability, low power efficiency, short life time, etc., which hindered the commercialization of organic optoelectronic devices.

There continues to be a need for organic optoelectronic materials which having good thermal stability and more efficient and long half-life time for organic optoelectronic device.

SUMMARY OF THE INVENTION

Provided an organic optoelectronic material can use for organic EL device, OPV device or OTFT device. The compound can overcome the drawbacks of the prior materials such as US20140131664A1, US20140175384A1, US20140209866A1, JP2012191017, U.S. Pat. No. 8,232, 546B2, DE102011089351A1 like as lower thermal stability, lower half-lifetime and higher power consumption.

An object of the present invention is to provide the compound which can be used as electron blocking material, emitting host material, hole blocking material and electron transporting material for organic EL device.

An object of the present invention is to provide the compound which can be used as hole transporting material or active layer material for OPV device.

An object of the present invention is to provide the compound which can be used as organic semiconductor layer material for OTFT device.

The present invention has the economic advantages for industrial practice. Accordingly the present invention, the organic optoelectronic material which can be used for organic EL, OPV, and OTFT device is disclosed. The mentioned the organic optoelectronic material is represented by the following formula (1):

formula (1)

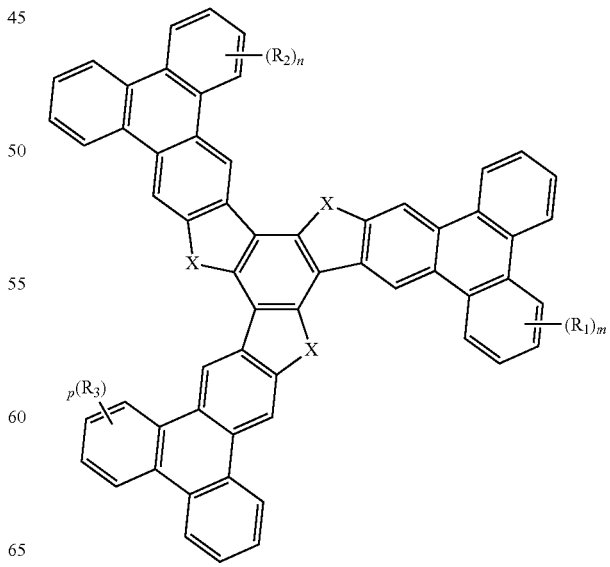

wherein X independently represents a divalent bridge selected from the atom or group consisting from O, S, C(R₄)(R₅) and NR₆, R₄ to R₆ are substituents; m, n and p independently represent an integer of 0 to 10, R₁ to R₃ are independently selected from the group consisting of a hydrogen atom, a halide, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms and a substituted or unsubstituted heteroaryl group having 3 to 50 carbon atoms.

DESCRIPTION OF THE PREFERRED EMBODIMENTS

Figure 1:
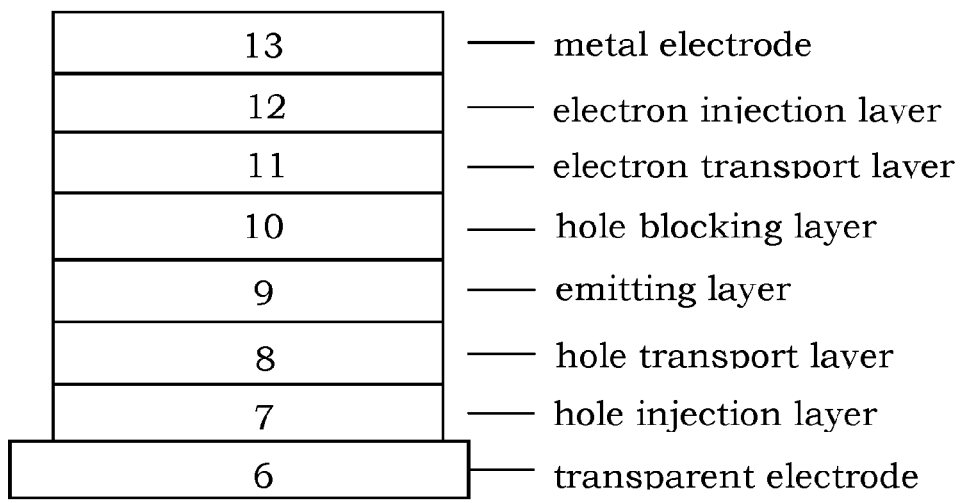
FIG. 1 show one example of organic EL device in the present invention, 6 is transparent electrode, 13 is metal electrode, 7 is hole injection layer which is deposited onto 6, 8 is hole transport layer which is deposited onto 7, 9 is fluorescent or phosphorescent emitting layer which is deposited onto 8, 10 is hole blocking layer which is deposited onto 9, 11 is electron transport layer which is deposited onto 10, 12 is electron injection layer which is deposited on to 11.

What probed into the invention is the organic optoelectronic material and organic EL device, OPV device or OTFT device using the organic optoelectronic material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the organic optoelectronic material which can be used for organic EL device, OPV device or OTFT device are disclosed. The mentioned organic optoelectronic material are represented by the following formula (1):

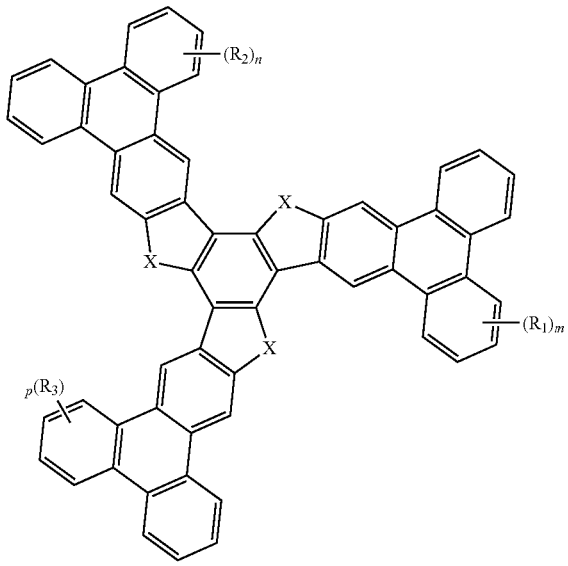

formula (1)

wherein X independently represents a divalent bridge selected from the atom or group consisting from O, S, C(R₄)(R₅) and NR₆, R₄ to R₆ are substituents; m, n and p represent an integer of 0 to 10, R₁ to R₃ are independently selected from the group consisting of a hydrogen atom, a halide, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms and a substituted or unsubstituted heteroaryl group having 3 to 50 carbon atoms.

The organic optoelectronic material according to above-mentioned formula (1), the material preferably use for organic EL device is represented by the following formula (2):

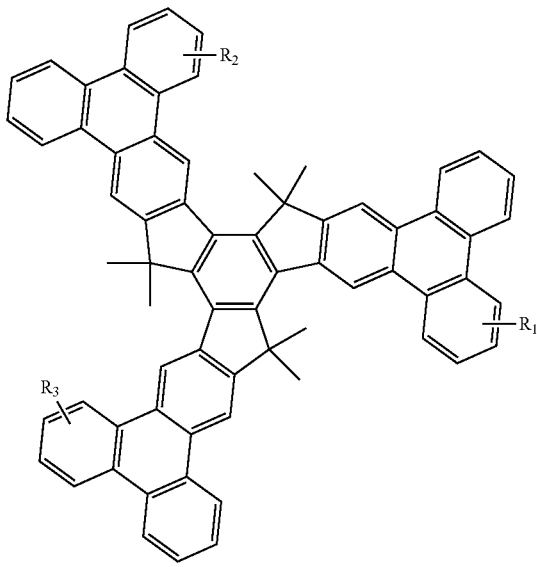

formula (2)

wherein R₁ to R₃ are independently selected from the group consisting of a hydrogen atom, a halide, a substituted or unsubstituted alkyl group having 1 to 20 carbon atoms, a substituted or unsubstituted aryl group having 6 to 50 ring carbon atoms, a substituted or unsubstituted aralkyl group having 6 to 50 carbon atoms and a substituted or unsubstituted heteroaryl group having 3 to 50 carbon atoms.

The organic optoelectronic material according to abovementioned formula (1), the material preferably use for OPV device is represented by the following formula (3):

formula (3)

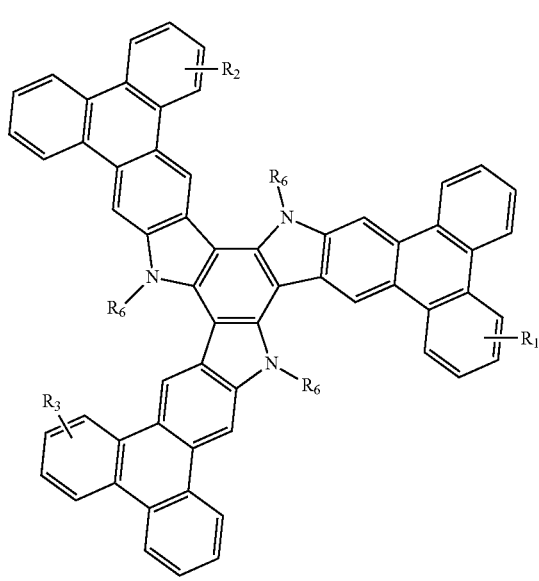

wherein $R_1$ to $R_3$ and $R_6$ are independently selected from the group consisting of a hydrogen atom, a halide, a substituted or unsubstituted alkyl group having 1 to 20 carbon atoms, a substituted or unsubstituted aryl group having 6 to 50 ring carbon atoms, a substituted or unsubstituted aralkyl group having 6 to 50 carbon atoms and a substituted or unsubstituted heteroaryl group having 3 to 50 carbon atoms.

The organic optoelectronic material according to abovementioned formula (1), the material preferably use for OTFT device is represented by the following formula (4):

formula (4)

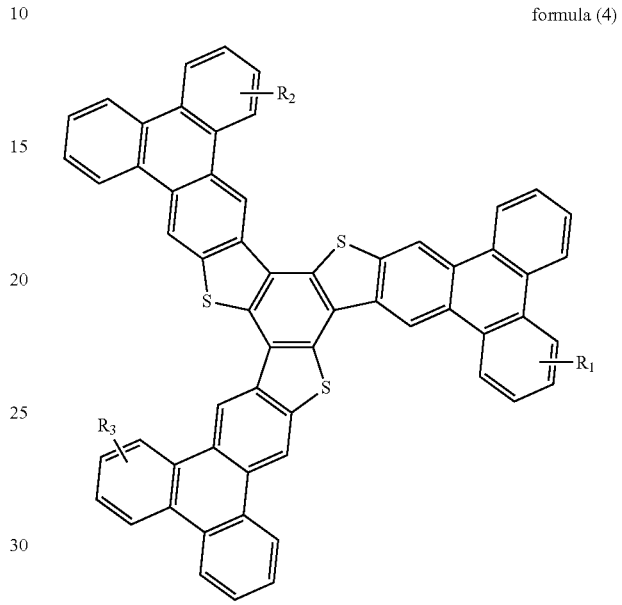

wherein $R_1$ to $R_3$ are independently selected from the group consisting of a hydrogen atom, a halide, a substituted or unsubstituted alkyl group having 1 to 20 carbon atoms, a substituted or unsubstituted aryl group having 6 to 50 ring carbon atoms, a substituted or unsubstituted aralkyl group having 6 to 50 carbon atoms and a substituted or unsubstituted heteroaryl group having 3 to 50 carbon atoms.

Specific example of the organic optoelectronic material are represented by the general formula (2) to (4) include the following compounds:

Ex1

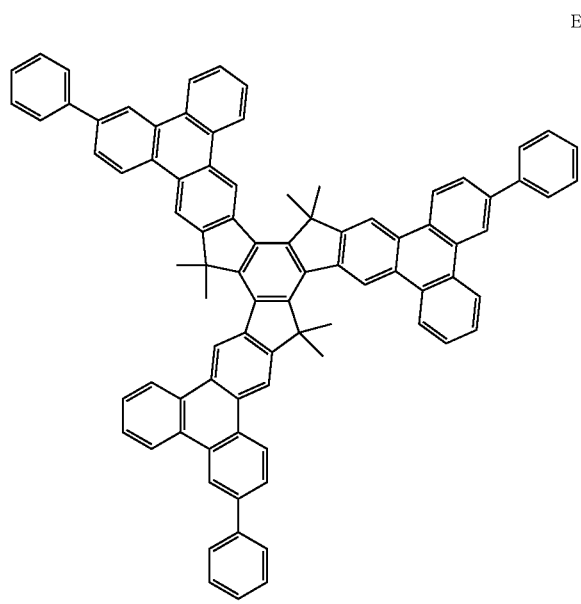

Ex2

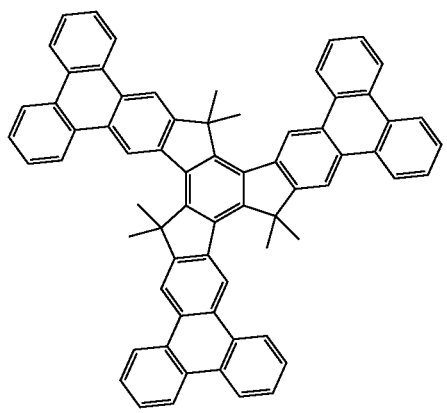

-continued
Ex3
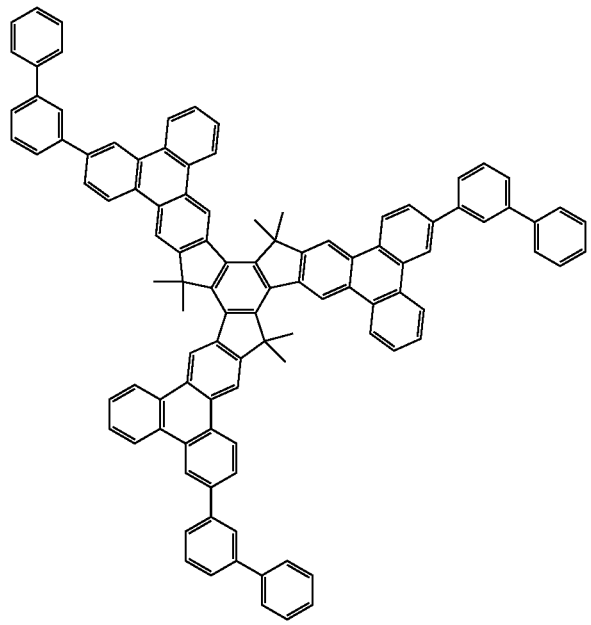
Ex4
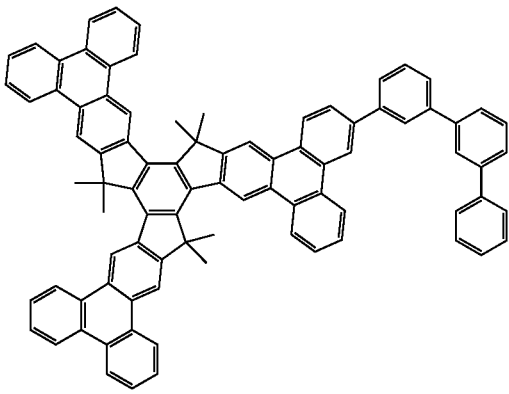
Ex5
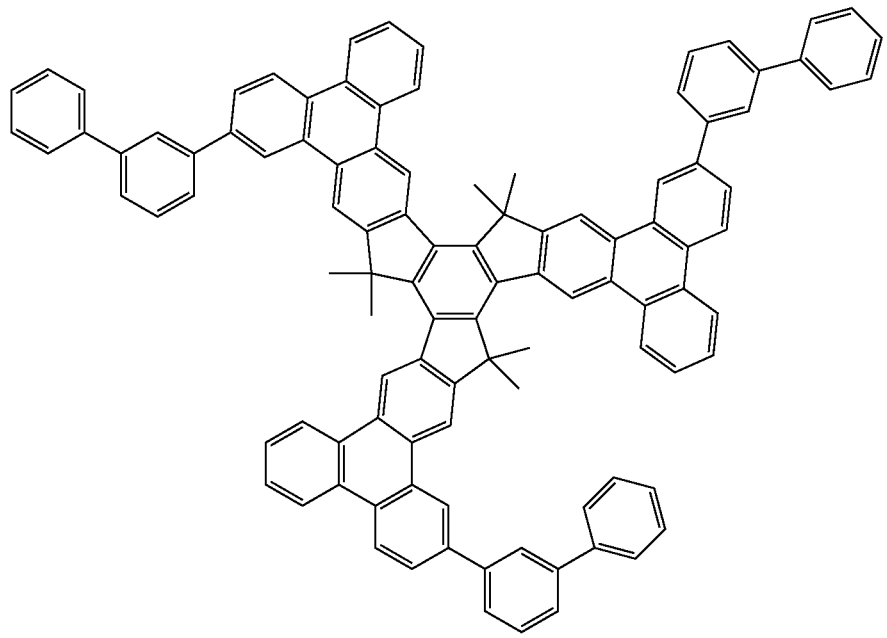

Ex6
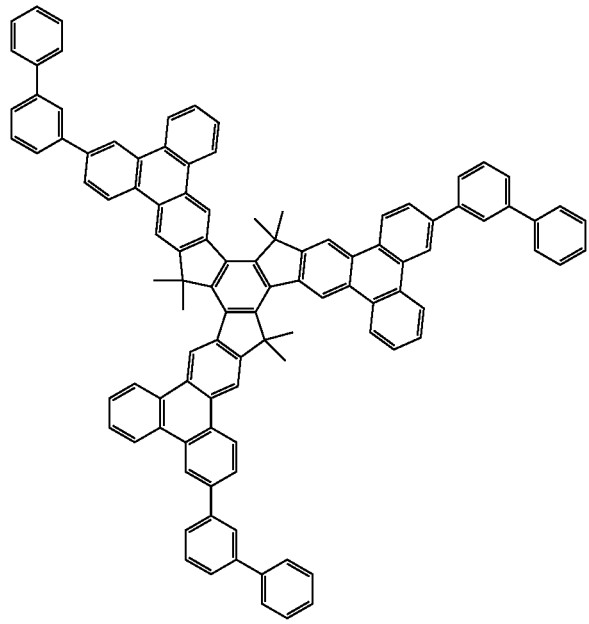
Ex7
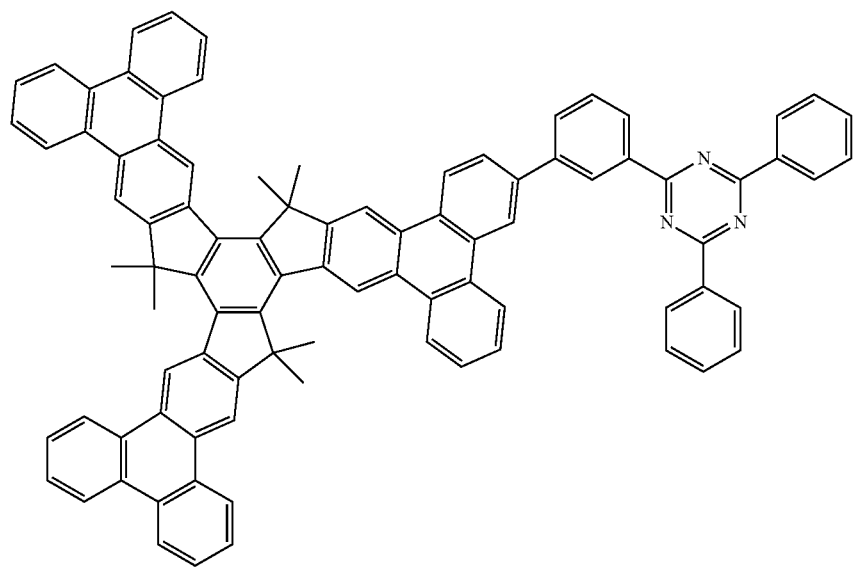

-continued
Ex8
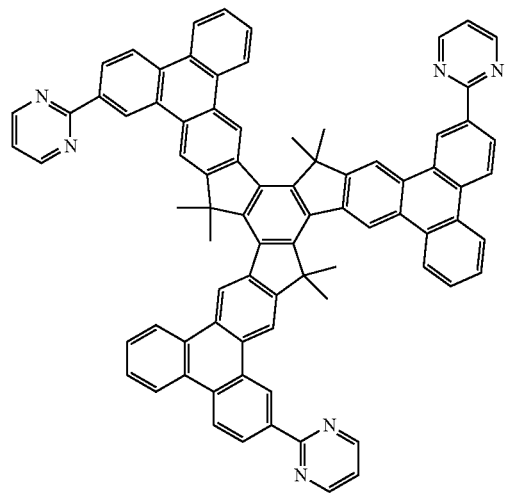
Ex9
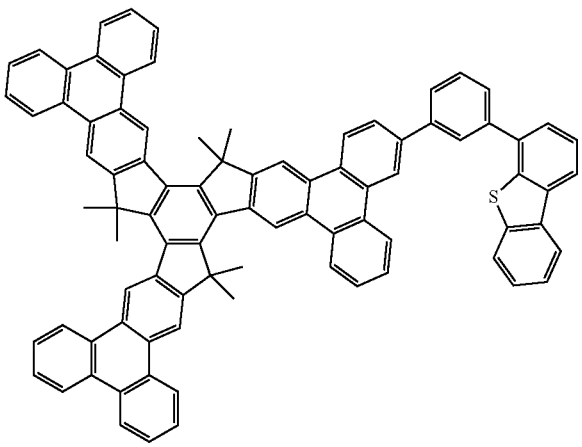
Ex10
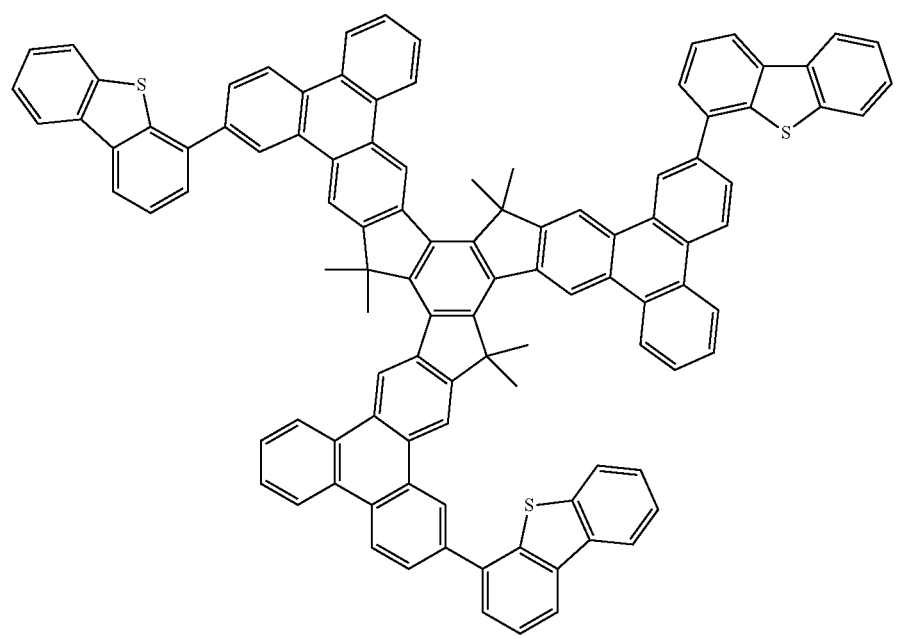

Ex11
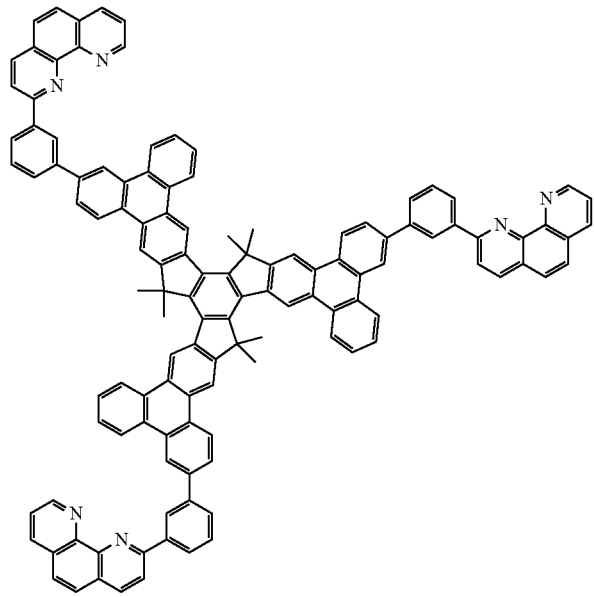
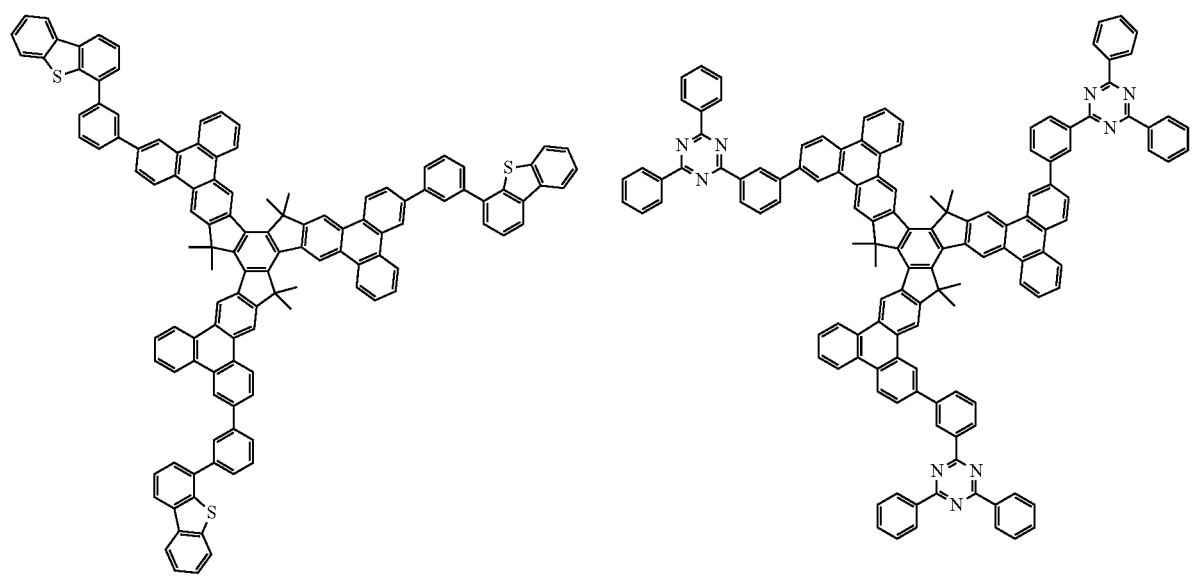

-continued
Ex14
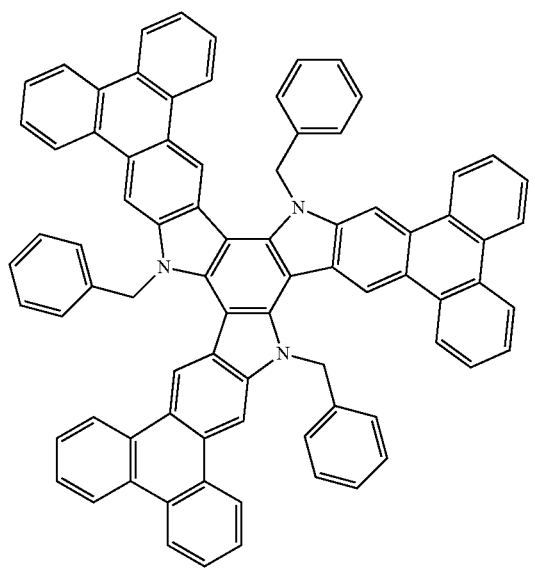
Ex15
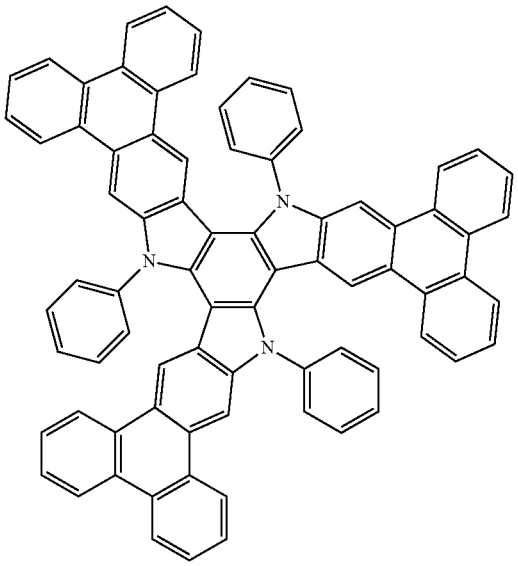
Ex16
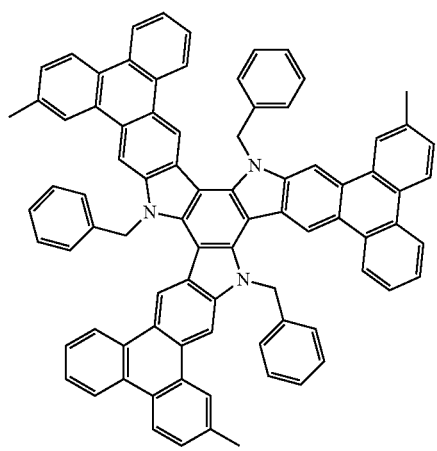
Ex17
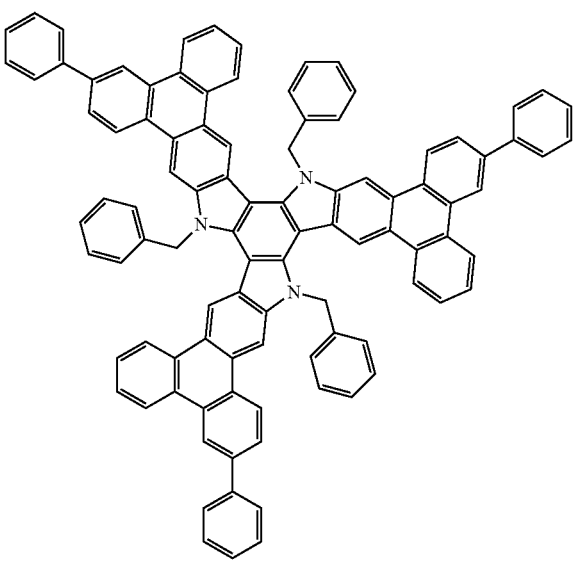

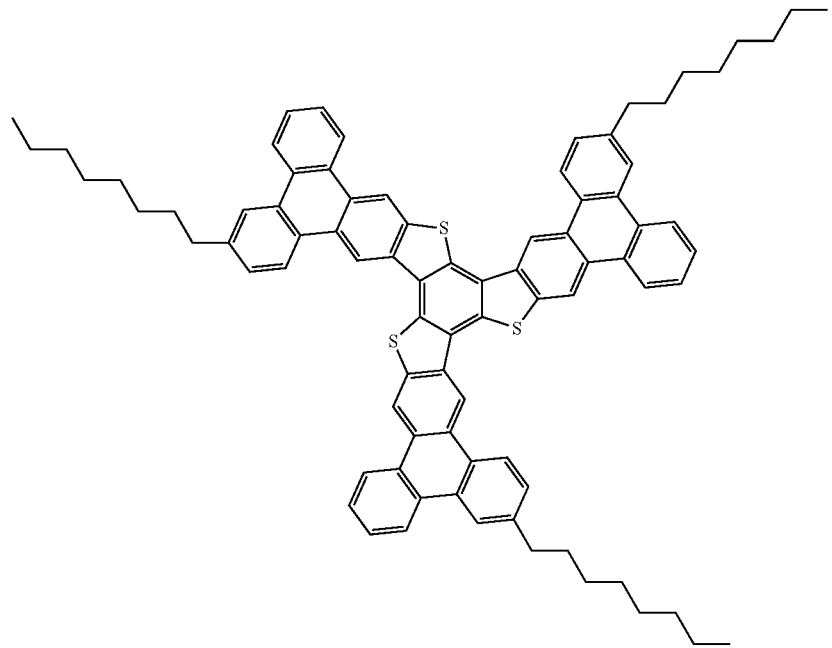
Ex18
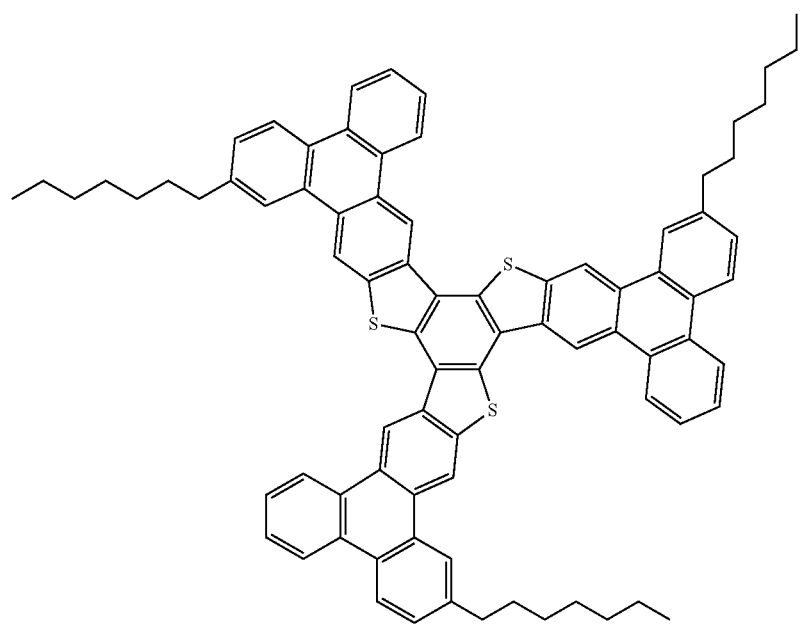
Ex19

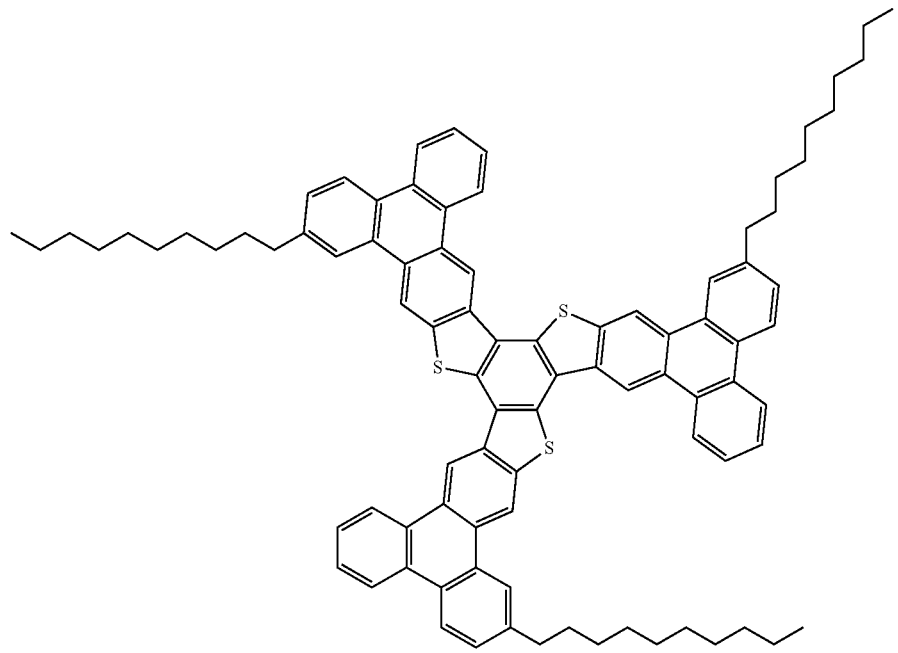

Ex20

Detailed preparation the organic optoelectronic material for the in the present invention could be clarified by exemplary embodiments, but the present invention is not limited to exemplary embodiments. EXAMPLE 1~3 show the preparation for organic optoelectronic material in the present invention. EXAMPLE 4~6 show the fabrication of organic EL device, OPV device and OTFT device and the characteristics.

Example 1

Synthesis of EX2

Synthesis of 5,5,10,10,15,15-hexamethyl-10,15-dihydro-5H-diindeno[1,2-a:1',2'-c]fluorene 150 ml of acetic acid anhydrous was dropwised slowly to a mixture of 28.7 g (21.7 mmol) of 1-indanone and 78 ml conc. HCl at ice-bath, then reflux overnight. After finishing the reaction, the mixture was allowed to cool to room temperature. The reaction was filtered to get the crude, the washed by water, acetone, dichloromethane to get compound as white solid (22.2 g, 15.6 mmol, 72%). $^1$H NMR (CDCl$_3$, 400 MHz): chemical shift (ppm) 7.96 (d, 3H), 7.70 (d, 3H), 7.51 (t, 3H), 7.41 (t, 3H), 4.28 (s, 6H).

Synthesis of 3,8,13-tribromo-5,5,10,10,15,15-hexamethyl-10, 15-dihydro-5H-diindeno[1,2-a:1',2'-c]fluorene

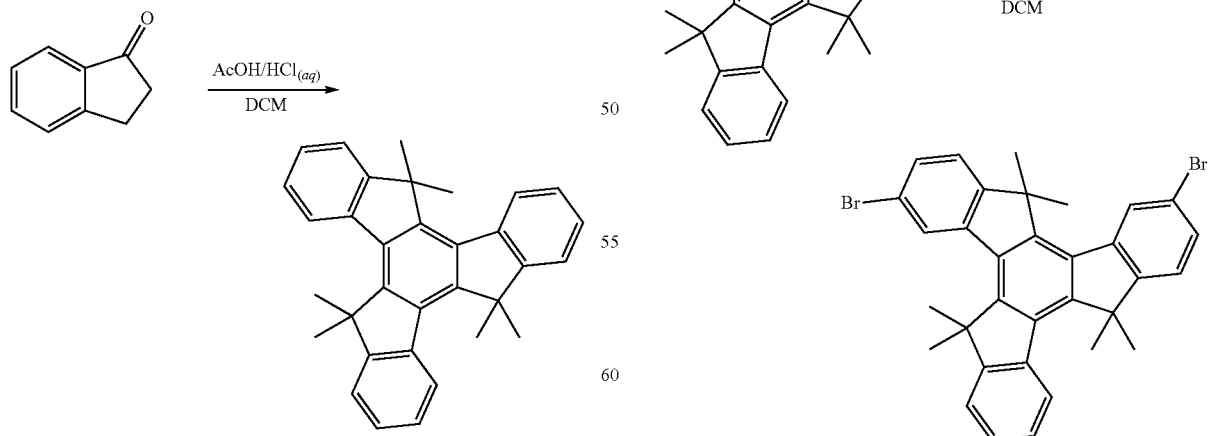

3.92 g (24.5 mmol) of bromine was dropwised slowly to a mixture of 3 g (7.0 mmol) of 5,5,10,10,15,15-hexamethyl- 10,15-dihydro-5H-diindeno [1,2-a:1',2'-c]fluorene and 150 ml dichloromethane at ice-bath, then stir at room temperature for 12 h. After finishing the reaction, the mixture was extracted with dichloromethane and water, the organic layer was washed with sodium sulfite aqueous solution, dried with anhydrous magnesium sulfate, the solvent was removed and the residue was recrystallized with THF to get the crude (3.0 g, 4.6 mmol, 66%). $^1$H NMR(CDCl$_3$, 400 MHz): chemical shift (ppm) 8.10 (d, 3H), 7.64 (d, 3H), 7.52 (dd, 3H), 1.81 (s, 18H).

Synthesis of 3,8,13-tri(biphenyl-2-yl)-5,5,10,10,15,15-hexamethyl-10,15-dihydro-5H-diindeno[1,2-a:1',2'-c]fluorene

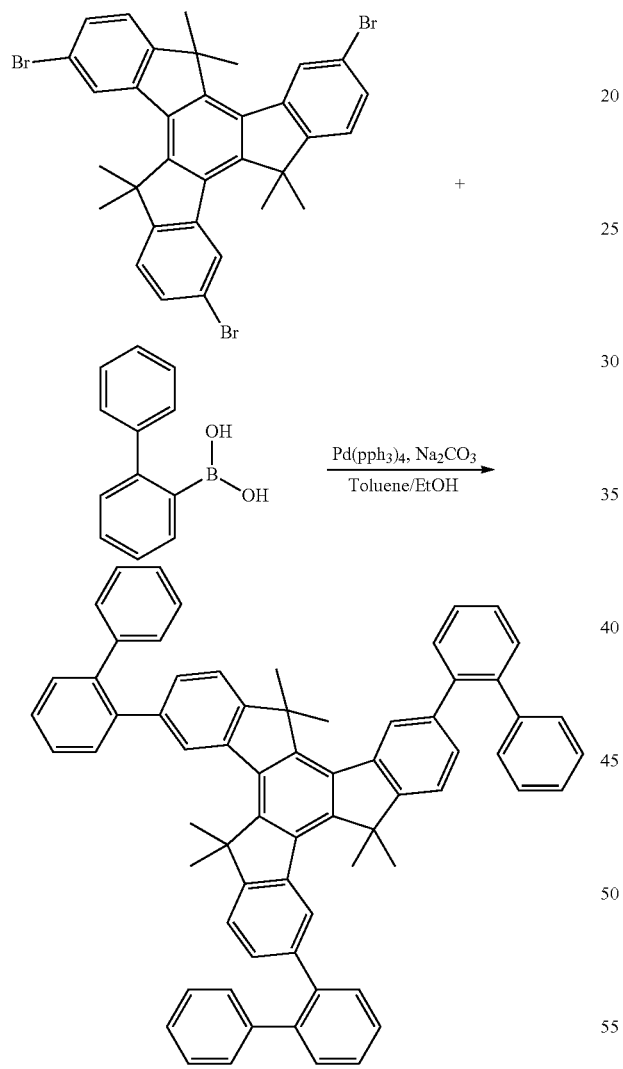

A mixture of 2 g (3.0 mmol) of 3,8,13-tribromo-5,5,10,10,15,15-hexamethyl-10,15-dihydro-5H-diindeno[1,2-a:1',2'-c]fluorene, 2.67 g (13.5 mmol) of biphenyl-2-ylboronic acid, 0.03 g (0.03 mmol) of Pd(PPh$_3$)$_4$, 7.5 ml of 2M Na$_2$CO$_{3(aq)}$, 13 ml of EtOH and 40 ml Toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (2.21 g, 2.06 mmol, 55%) as a white solid. $^1$H NMR (CDCl$_3$, 400 MHz): chemical shift (ppm) 8.15 (d, 3H), 7.85~7.65 (m, 15H), 7.52~7.24 (m, 15H), 1.81 (s, 18H). MS (m/z, FD$^+$): 882.7

Synthesis of EX2

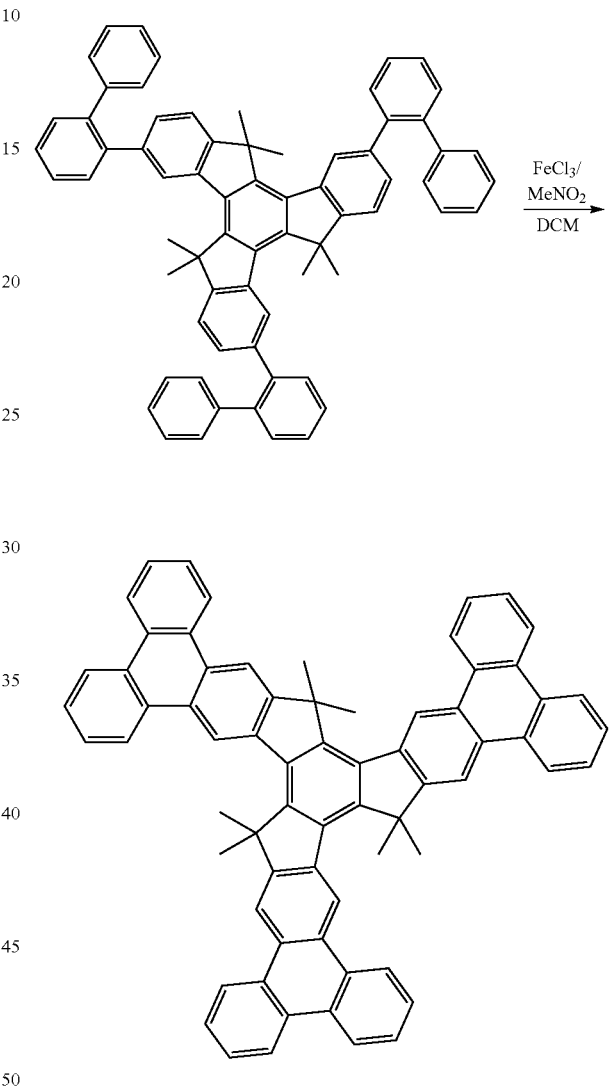

In a 100 ml three-necked flask that had been degassed and filled with nitrogen, 1 g (1.13 mmol) of 3,8,13-tri(biphenyl-2-yl)-5,5,10,10,15,15-hexamethyl-10,15-dihydro-5H-diindeno[1,2-a:1',2'-c]fluorene was dissolved in anhydrous dichloromethane (22.5 ml), 1.83 g (11.3 mmol) of iron(III) chloride and 2.23 ml of nitromethane were dropwised into the reactor at ice bath, and the mixture was stirred until the starting material disappeared. The reaction was quenched with 30 ml methanol and filtered to get the crude. The crude was purified by column chromatography on silica, then recrystallized twice with dichloromethane/hexane to afforded EX2 as a white solid (0.34 g, 0.39 mmol, 35%). $^1$H NMR(CDCl$_3$, 400 MHz): chemical shift (ppm) 9.11 (s, 3H), 8.86~8.91 (m, 6H), 8.83 (s, 3H), 8.80 (d, 3H), 8.66 (d, 3H), 7.85~7.45 (m, 12H), 1.81 (s, 18H). MS (m/z, FD$^+$): 877.1

Example 2

Synthesis of EX14

Synthesis of 5,10,15-tribenzyl-3,8,13-tribromo-10,15-dihydro-5H-diindolo[3,2-a:3',2'-c]carbazole

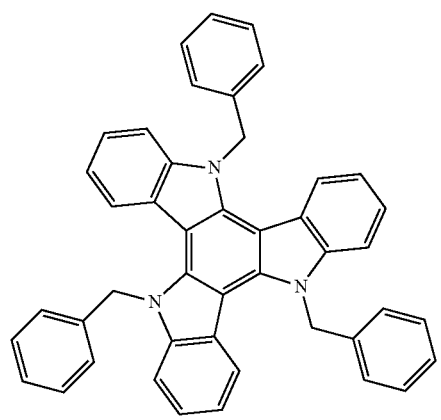

Synthesis of 5,10,15-tribenzyl-3,8,13-tri(biphenyl-2-yl)-10,15-dihydro-5H-diindolo[3,2-a:3',2'-c]carbazole

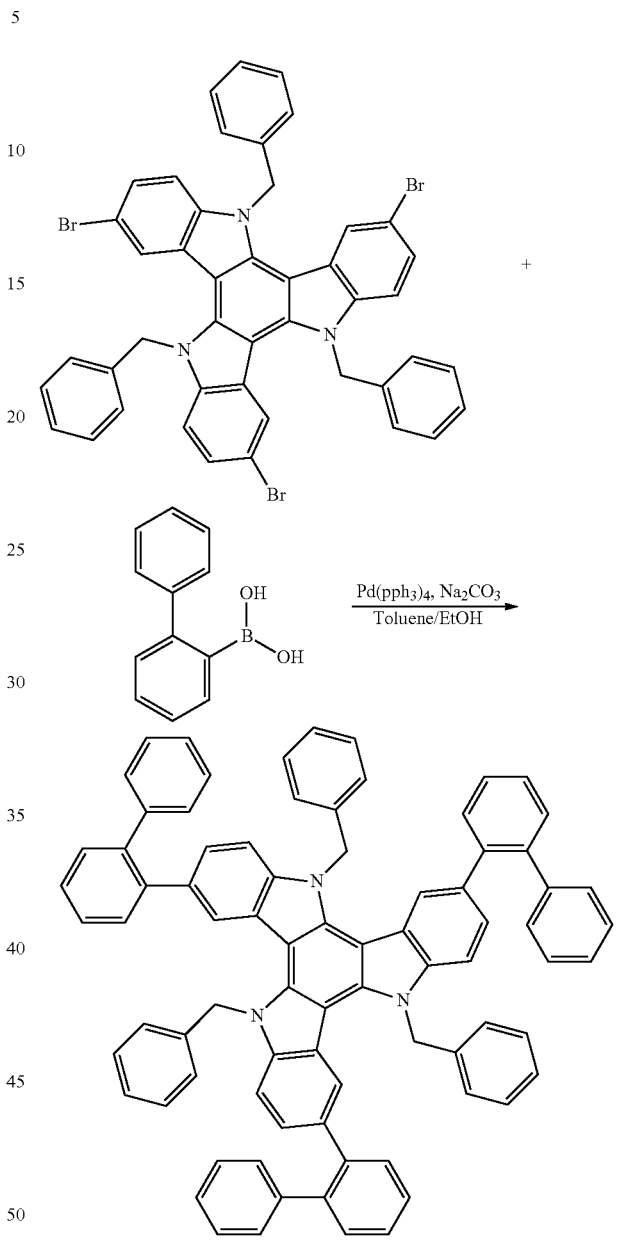

2.86 g (16.09 mmol) of N-Bromosuccinimide was added to a mixture of 3 g (4.87 mmol) of 5,10,15-tribenzyl-10,15-dihydro-5H-diindolo [3,2-a:3',2'-c]carbazole (J. Mater. Chem. A, 2013, 1, 4077) and 300 ml DMF at dark, and then slowly heated until 60° C., then keep for 12 h. After finishing the reaction, the mixture was allowed to cool to room temperature and poured into ice-water, then filtered to get the crude (3.2 g, 3.79 mmol, 78%) as a pale brown solid, used in next step without purification. $^1$H NMR(CDCl$_3$, 400 MHz): chemical shift (ppm) 8.02 (m, 3H), 7.76 (s, 3H), 7.47~7.11 (m, 15H), 6.01 (s, 6H).

A mixture of 3.2 g (3.75 mmol) of 5,10,15-tribenzyl-3,8,13-tribromo-10,15-dihydro-5H-diindolo[3,2-a:3',2'-c]carbazole, 3.34 g (16.90 mmol) of biphenyl-2-ylboronic acid, 0.04 g (0.01 mmol) of Pd(PPh$_3$)$_4$, 9.3 ml of 2M Na$_2$CO$_{3(aq)}$, 15 ml of EtOH and 45 ml Toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to get product (2.21 g, 2.06 mmol, 55%) as a white solid. MS (m/z, MALDI-TOF): 1071.2

Synthesis of EX14

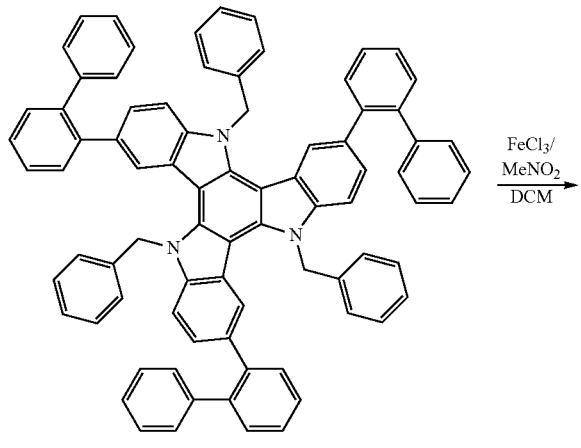

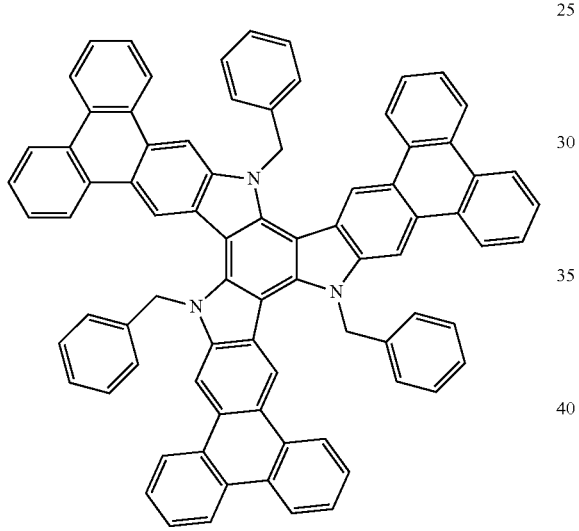

In a 100 ml three-necked flask that had been degassed and filled with nitrogen, 1 g (0.93 mmol) of 5,10,15-tribenzyl-3,8,13-tri(biphenyl-2-yl)-10,15-dihydro-5H-diindolo[3,2-a:3',2'-c]carbazole was dissolved in anhydrous dichloromethane (18.6 ml), 1.50 g (9.3 mmol) of iron(III) chloride and 1.84 ml of nitromethane were dropwised into the reactor at ice bath, and the mixture was stirred until the starting material disappeared. The reaction was quenched with 30 ml methanol and filtered to get the crude. The crude was purified by column chromatography on silica, then recrystallized twice with dichloromethane/hexane to afforded EX14 as a off-white solid (0.21 g, 0.20 mmol, 22%). $^1$H NMR(CDCl$_3$, 400 MHz): chemical shift (ppm) 9.08 (s, 3H), 8.53~8.46 (m, 6H), 8.34 (s, 3H), 8.34 (dd, 3H), 7.99 (dd, 3H), 7.83 (m, 3H), 7.61~7.29 (m, 24H), 6.22 (s, 6H). MS (m/z, FD$^+$): 1066.1

Example 3

Synthesis of EX18

Synthesis of 2,7,12-tribromo-benzo[1,2-b:3,4-b':5,6-b"]tris[1]benzothiophene

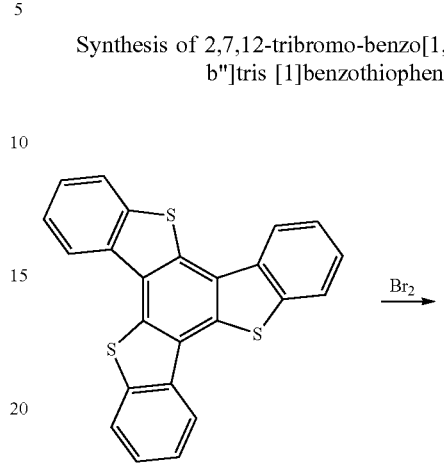

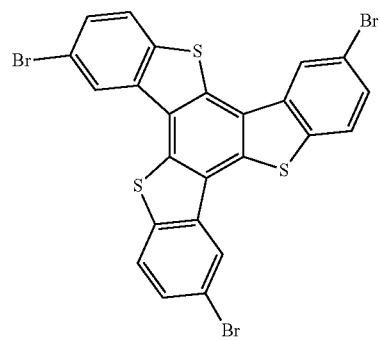

Benzo[1,2-b:3,4-b':5,6-b"]tris[1]benzothiophene (The prepared method from Tetrahedron, 42(2), 763-73; 1986) instead of 5,5,10,10,15,15-hexamethyl-10,15-dihydro-5H-diindeno[1,2-a:1',2'-c]fluorene, except for using the same method as in synthesis Example 1, the desired compound of 2,7,12-tribromo-benzo[1,2-b:3,4-b':5,6-b"]tris[1]benzothiophene (yield=52%) was obtained. MS (m/z, FD+): 629.9

Synthesis of 2,7,12-tri(5-octyl biphenyl-2-yl)-benzo[1,2-b:3,4-b':5,6-b"]tris[1]benzothiophene

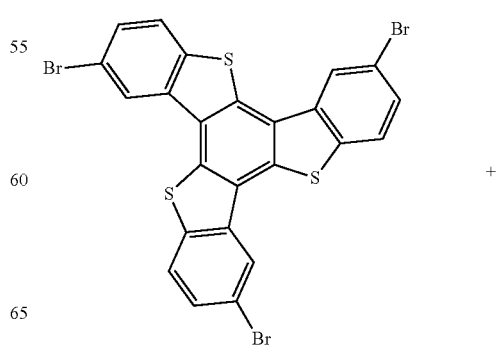

+

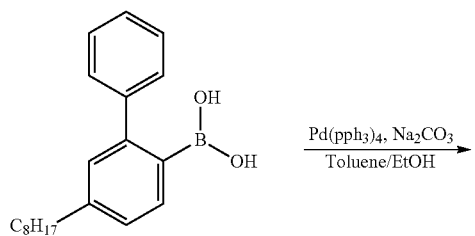

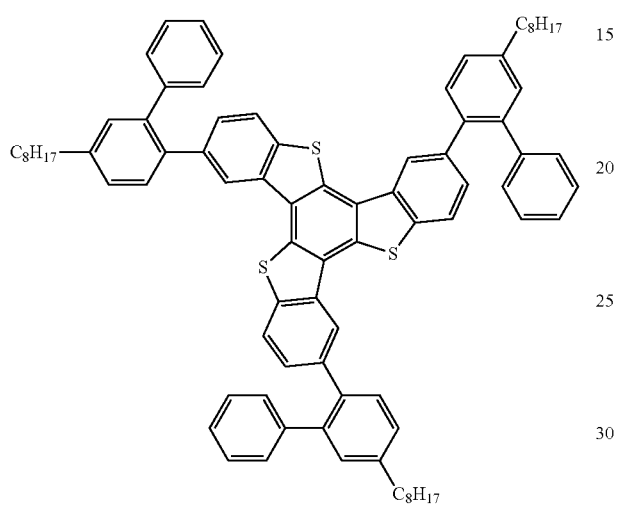

2,7,12-tribromo-benzo[1,2-b:3,4-b':5,6-b"]tris[1]benzothiophene instead of 3,8,13-tribromo-5,5,10,10,15,15-hexamethyl-10,15-dihydro-5H-diindeno[1,2-a:1',2'-c]fluorene and 5-octylbiphenyl-2-ylboronic acid instead of biphenyl-2-ylboronic acid, except for using the same method as in synthesis Example 1, the desired compound of 2,7,12-tri(5-octyl biphenyl-2-yl)-benzo [1,2-b:3,4-b':5,6-b"]tris[1]benzothiophene (yield=58%) was obtained. MS (m/z, FD+): 1190.2

Synthesis of EX18

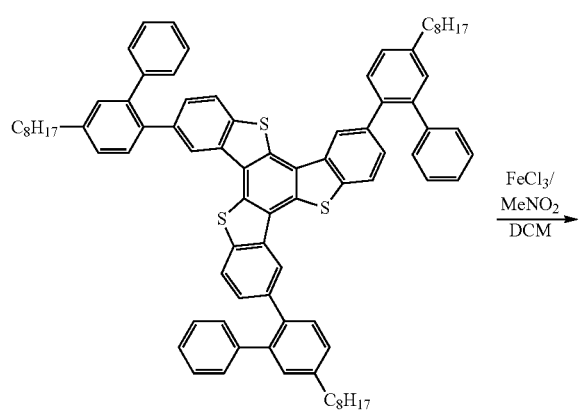

2,7,12-tri(5-octyl biphenyl-2-yl)-benzo[1,2-b:3,4-b':5,6-b"]tris[1] benzothiophene instead of 3,8,13-tri(biphenyl-2-yl)-5,5,10,10,15,15-hexamethyl-10,15-dihydro-5H-diindeno[1,2-a:1',2'-c]fluorene, except for using the same method as in synthesis Example 1, the desired EX18 (yield=24%) was obtained. MS (m/z, FD+): 1182.9

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 1000).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine (NPB) is most widely used as the hole transporting layer, 4-(10,10-dimethyl-10H-indeno[2,1-b]triphenylen-13-yl)dibenzo[b,d]thiophene (H1) and 10,10-dimethyl-13-(3-(triphenylen-2-yl)phenyl)-10H-indeno[2,1-b]triphenylene(H2) are used as phosphorescent host for comparable material in this invention for organic EL device. 2-(10,10-dimethyl-10H-indeno[2,1-b]triphenylen-13-yl)-4,6-bis-5-phenylbiphenyl-3-yl)-1,3,5-triazine (ET3) is used as electron transporting material to co-deposit with 8-hydroxyquinolato-lithium (LiQ) in organic EL device. Tris(2-phenylpyridinato)iridium(III) (D2) is used as phosphorescent dopant. The prior art of OLED materials for producing standard organic EL device control and comparable material in this invention shown its chemical structure as following structure:

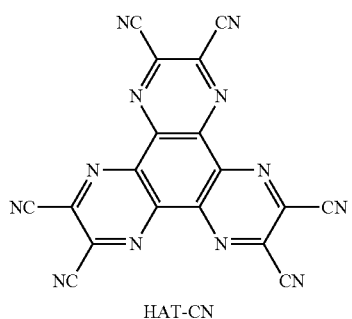

HAT-CN

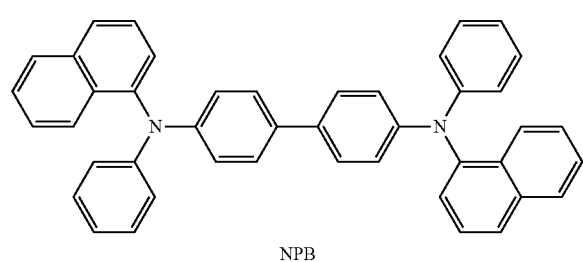

NPB

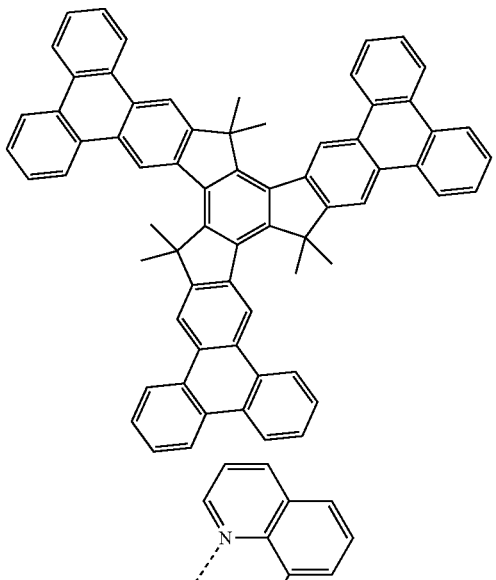

Ex2

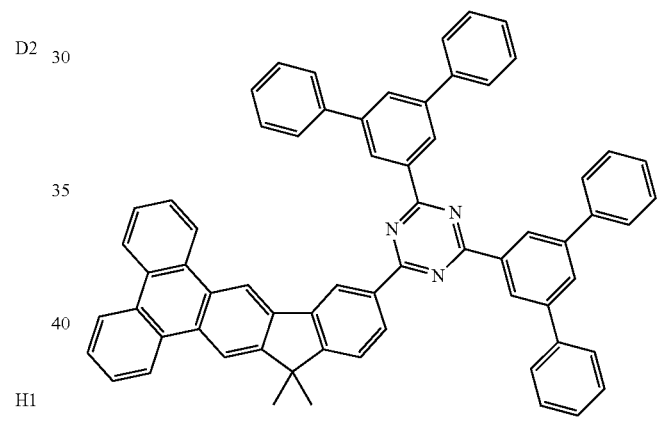

LiQ

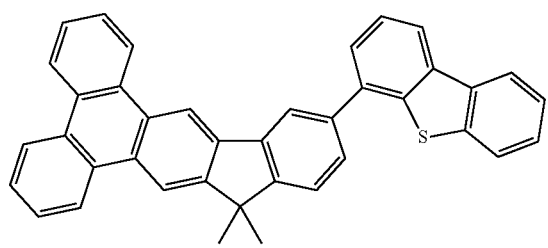

D2

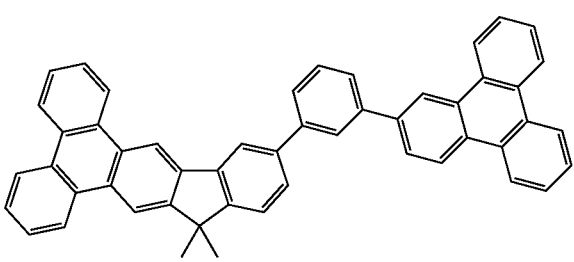

H1

ET3

H2

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 4

Using a procedure analogous to the above mentioned general method, phosphorescent emitting organic EL device having the following device structures are produced (See FIG. 1.): Device I: ITO/HAT-CN (20 nm)/NPB (110 nm)/ Phosphorescent Host (PhHost) doped 12% D2 (35 nm)/Hole Blocking Material (HBM)(10 nm)/ET3 co-deposit 50% LiQ (40 nm)/LiQ (1 nm)/Al (160 nm). The I-V-B, Efficiency (at 1000 nits) and half-life time of phosphorescent emitting organic EL device testing report as Table 1. The half-life time is defined that the initial luminance of 3000 cd/m² has dropped to half.

TABLE 1

| PhHost | HBM | Voltage (V) | Efficiency (cd/A) | CIE (x, y) | Half-life time (hour) |
|---|---|---|---|---|---|
| H1 | H1 | 4.8 | 25 | 0.352, 0.608 | 650 |
| H2 | H2 | 5.5 | 22 | 0.358, 0.606 | 750 |
| Ex2 | Ex2 | 3.6 | 20 | 0.364, 0.614 | 1150 |

In the above preferred embodiments for organic EL device test report (see Table 1), we show that the optoelectronic material with a general formula (I) in the present invention display good performance and shown lower driving voltage and longer half-life time for organic EL device in the present invention.

General Method of Producing Organic Photovoltaics Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 1000).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

The current density/voltage (J-V) characteristics of this OPV device are taken with a Keithley 2400 programmable voltage-current source meter in the dark and under an illumination intensity of 100 mW/cm² with a calibrated AM 1.5 G sun.

Subphthalocyanine chloride (SubPc) or Subnaphthalocyanine chloride (SubNc) are used as donors in this OPV device, C60 or C70 is most widely used as an acceptor, and 2,9-dimethyl-4,7-diphenyl-1,10-phenanthroline (BCP) is used as an exciton blocking layer. The prior art of OPV materials for producing standard OPV device control and comparable material in this invention shown its chemical structure as following structure:

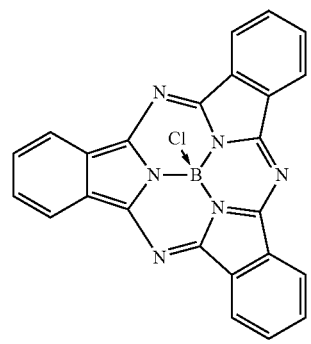

SubPC

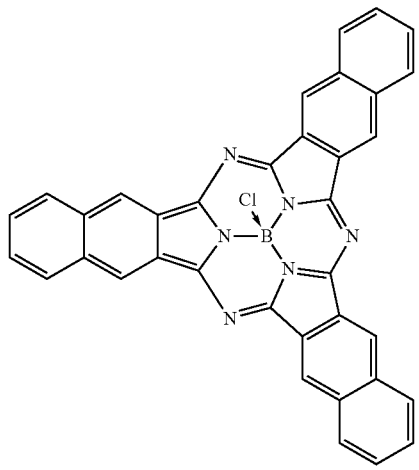

SubNC

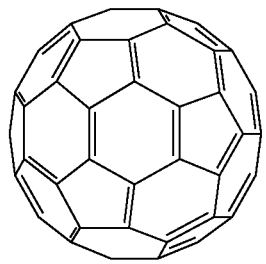

C60

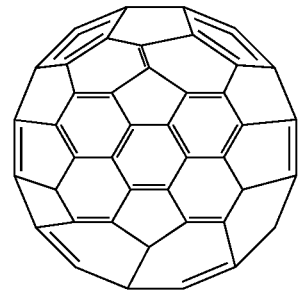

C70

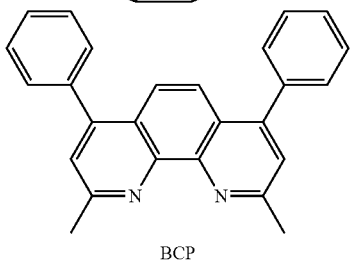

BCP

-continued

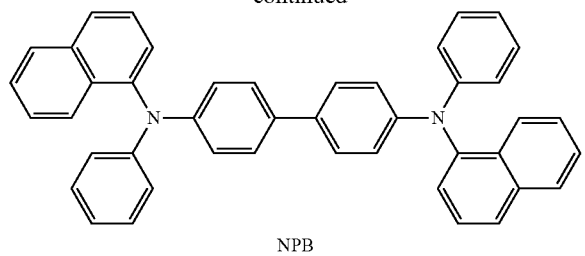

NPB

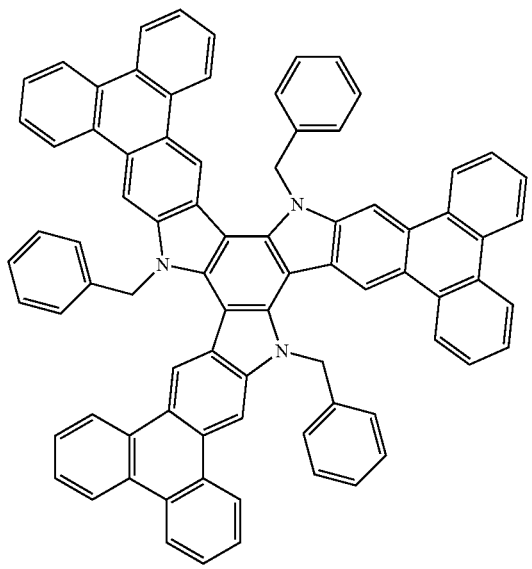

Example 5

Figure 2:
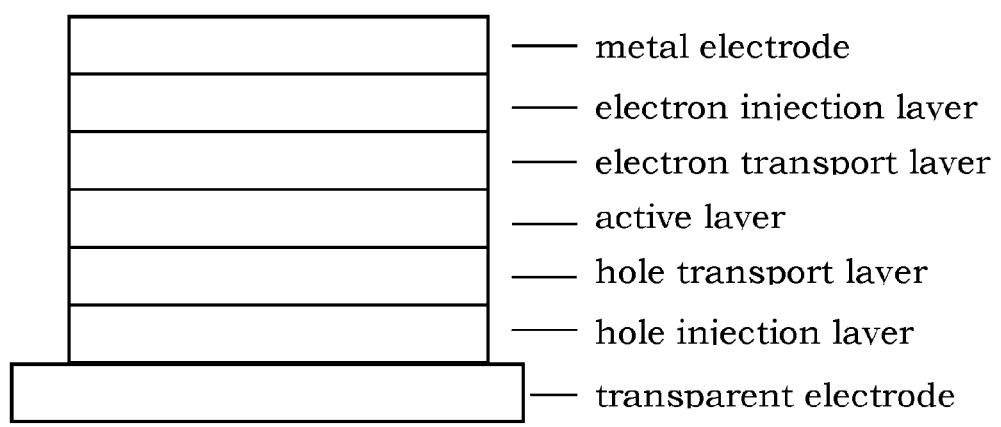
FIG. 2 show the drawing of OPV device in the present invention.

Using a procedure analogous to the above mentioned general method, OPV device having the following device structures are produced (See FIG. 2.): Device I: ITO/buffer layer/HTM (15 nm)/SubPC (20 nm)/C60 (30 nm)/BCP (10 nm)/LiF (1 nm)/Al (120 nm). The J-V, Efficiency and FF (%) of OPV device testing report are shown as Table 2.

TABLE 2

| HTM | $V_{OC}$ (V) | $J_{SC}$ (mA/cm$^2$) | FF (%) | Efficiency (%) |
|---|---|---|---|---|
| NPB | 0.92 | 5.6 | 48.4 | 2.8 |
| EX14 | 1.03 | 6.9 | 56.6 | 3.2 |
| — | 0.99 | 5.8 | 54.7 | 2.7 |

In the above preferred embodiments for OPV device test report (see Table 2), we show that the optoelectronic material with a general formula (I) in the present invention used as hole transport material (HTM) for OPV device display higher efficiency, FF % and shown higher $V_{OC}$ for OPV device in the present invention.

General Method of Producing Organic Thin-Film Transistors Device

The substrate of OTFT device in the present invention is p$^+$-doped Si with thermally grown 250 nm SiO$_2$. The deposition parameters for the sol-gel coated polymethyl methacrylate thin films on the SiO$_2$ gate oxide, its role as a surface modifying layer and the organic thin-film layer material deposition procedure are explained elsewhere. Ultrathin LiF layer was then deposited using thermal evaporation onto the organic thin-film material and the thickness of the LiF layer was varied from 1 to 10 Å. Finally, 60 nm thick aluminum was thermally evaporated onto the organic thin-film material through a shadow mask to form the S/D electrodes. The thickness of the films was monitored by using a quartz crystal monitor. The output characteristics of a device with a channel width of 20 cm and a length of 10 um exhibited typical FET characteristics.

The electrical measurements of the devices were performed in a nitrogen environment inside a glove box using HP 4156C and Keithley 4200 semiconductor parameter analyzer. The capacitance-voltage (C-V) measurement was performed by Agilent E4980A precision LCR meter.

The prior art of OTFT materials for producing standard OTFT device control and comparable material in this invention shown its chemical structure as following structure:

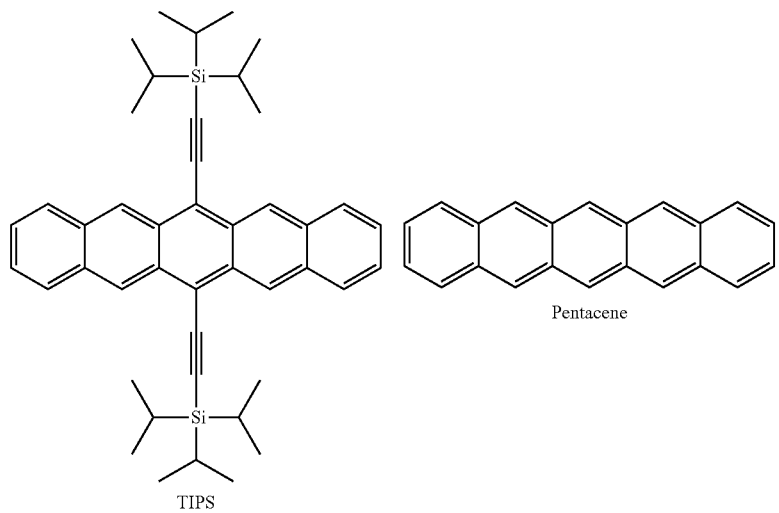

TIPS
Pentacene

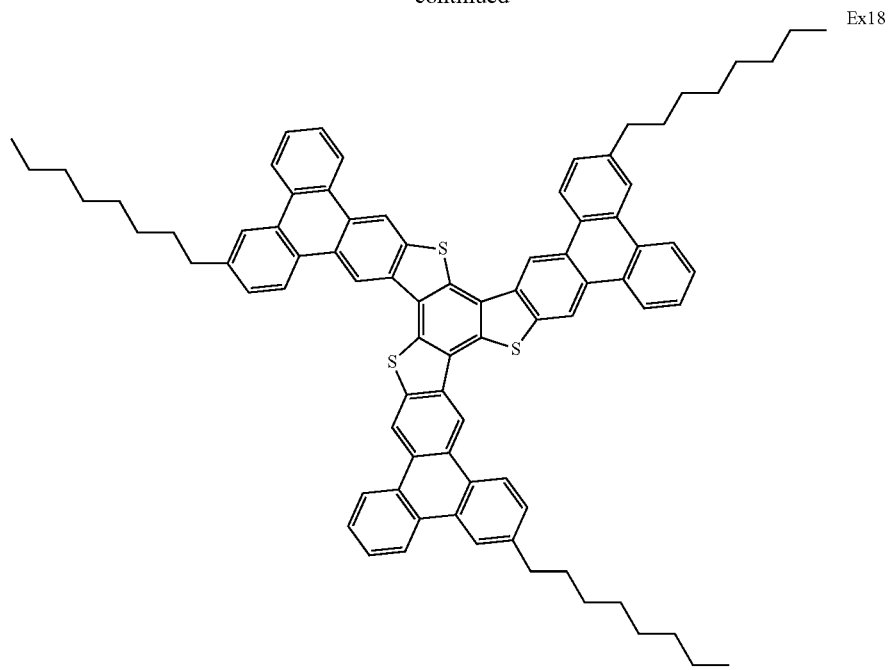

Ex18

Example 6

Figure 3:
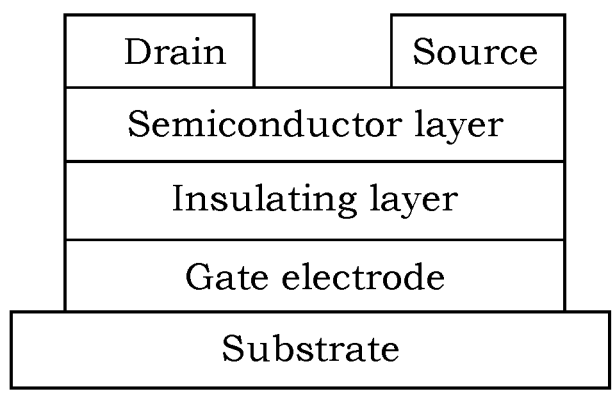
FIG. 3 show the drawing of OTFT device in the present invention.

Using a procedure analogous to the above mentioned general method, OTFT device having the following device structures as FIG. 3, organic thin-film material (EX18), comparable material (Pentacene and 6,13-Bis(tri isopropyl-silylethynyl)pentacene (TIPS)) were spin-coated or deposited over the device structure to respectively form a thin film. The field-effect carrier mobility and on/off current ratio of OTFT device data are shown as Table 3.

TABLE 3

|  | field-effect carrier mobility | on/off current ratio |
| --- | --- | --- |
| EX18 | $0.99 \times 10^{-1}$ cm$^2$ V$^{-1}$s$^{-1}$ | $1.6 \times 10^5$ |
| Pentacene | $1.3 \times 10^{-2}$ cm$^2$ V$^{-1}$s$^{-1}$ | $4.3 \times 10^4$ |
| TIPS | $1.1 \times 10^0$ cm$^2$ V$^{-1}$s$^{-1}$ | $3.9 \times 10^6$ |

In the above preferred embodiments for OTFT device test report (see Table 3), we show that the optoelectronic material with a general formula (I) in the present invention used as organic thin-film material for OTFT device display good performance shown the OTFT exhibited an on/off current ratio of about $1.6 \times 10^5$, and the apparent field-effect mobility was estimated to be $1.0 \times 10^{-1}$ cm$^2$ V$^{-1}$ s$^{-1}$.

To sum up, the present invention discloses an organic optoelectronic material which can be used for organic EL device, OPV device or OTFT device is disclosed. The mentioned organic optoelectronic material are represented by the following formula (1):

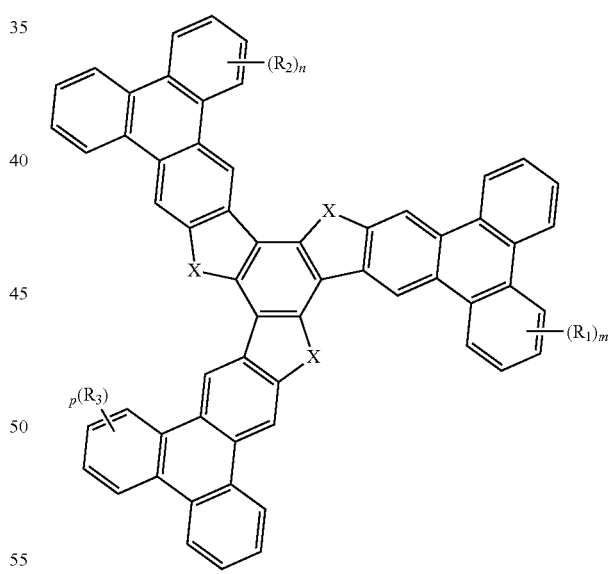

formula (1)

X independently represent a divalent bridge selected from the atom or group consisting from O, S, C(R$_4$)(R$_5$) and NR$_6$, R$_4$ to R$_6$ are substituents. m, n and p independently represent an integer of 0 to 10. R$_1$ to R$_3$ are independently selected from the group consisting of a hydrogen atom, a halide, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms, and a substituted or unsubstituted heteroaryl group having 3 to 50 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. An organic optoelectronic material represented by the following formula (1):

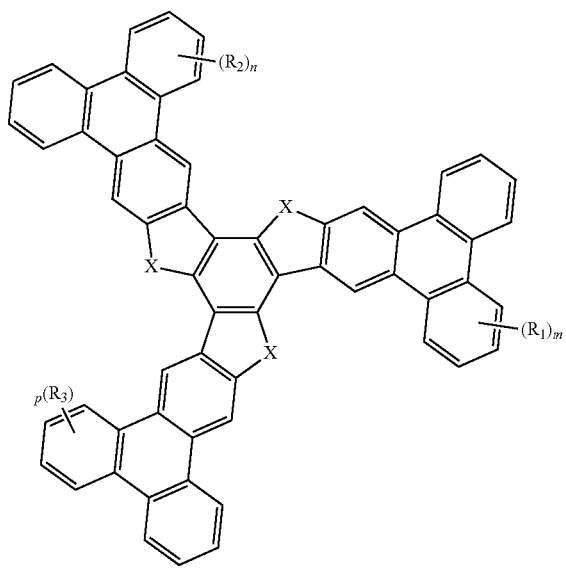

formula(1)

wherein X independently represents a divalent bridge selected from the atom or group consisting from O, S, $C(R_4)(R_5)$ and $NR_6$, m, n and p independently represent an integer of 0 to 10; $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 50 carbon atoms, a substituted or unsubstituted aralkyl group having 6 to 50 carbon atoms and a substituted or unsubstituted heteroaryl group having 3 to 50 carbon atoms; $R_4$ and $R_5$ are methyl; and $R_6$ is selected from the group consisting of a hydrogen atom, a halide, a substituted or unsubstituted aryl group having 6 to 50 ring carbon atoms, a substituted or unsubstituted aralkyl group having 6 to 50 carbon atoms and a substituted or unsubstituted heteroaryl group having 3 to 50 carbon atoms.

2. The organic optoelectronic material according to claim 1, having one of the following formula (2) to formula (4):

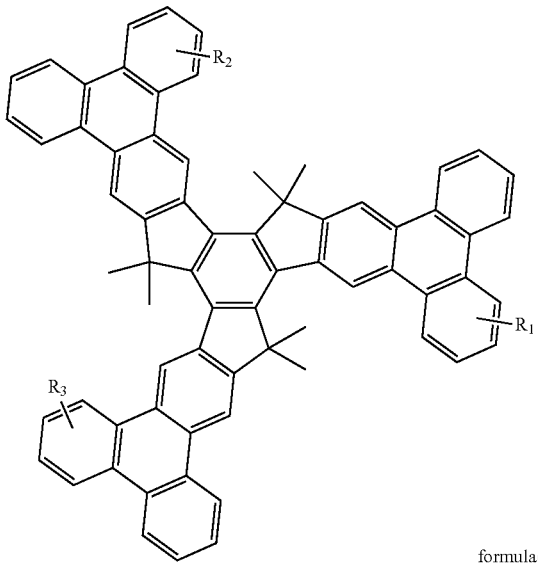

formula(2)

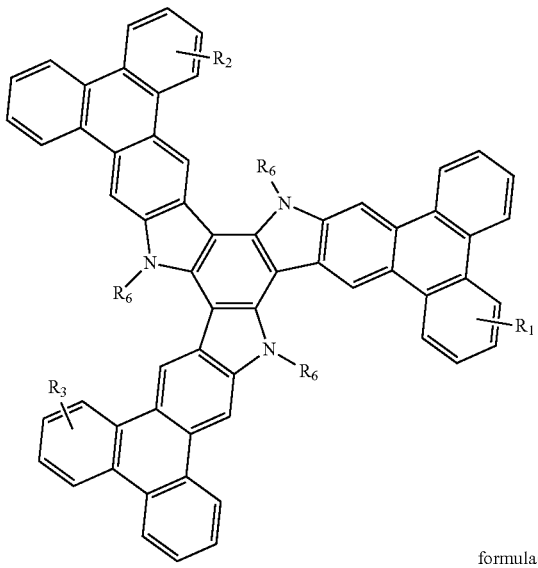

formula(3)

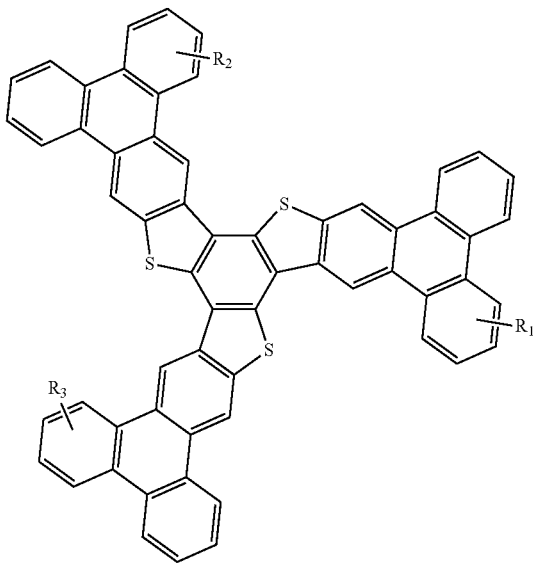

formula(4)

wherein $R_1$ to $R_3$ are independently selected from the group consisting of a hydrogen atom, a halide, a substituted or unsubstituted alkyl group having 1 to 20 carbon atoms, a substituted or unsubstituted aryl group having 6 to 50 ring carbon atoms, a substituted or unsubstituted aralkyl group having 6 to 50 carbon atoms and a substituted or unsubstituted heteroaryl group having 3 to 50 carbon atoms; and $R_6$ is selected from the group consisting of a hydrogen atom, a halide, a substituted or unsubstituted aryl group having 6 to 50 ring carbon atoms, a substituted or unsubstituted aralkyl group having 6 to 50 carbon atoms and a substituted or unsubstituted heteroaryl group having 3 to 50 carbon atoms.

3. The organic optoelectronic material according to claim 1, represented by one of the following formulae:

Ex1

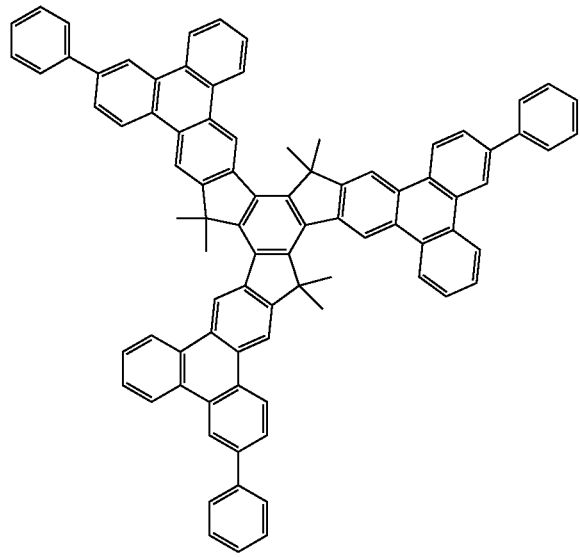

Ex2

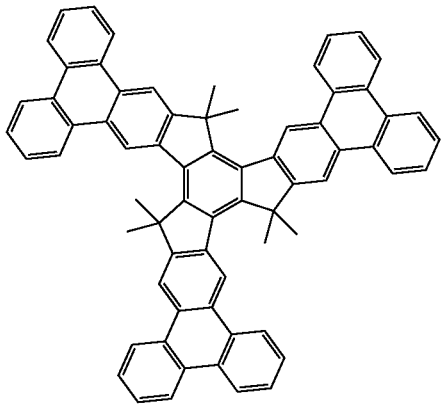

Ex3

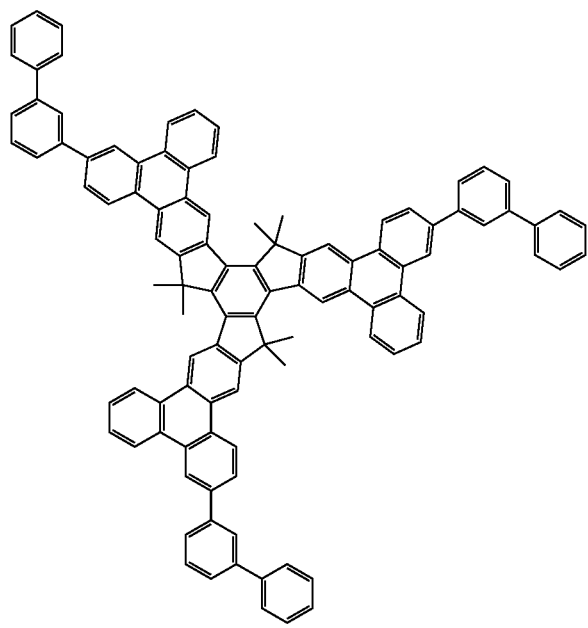

Ex4

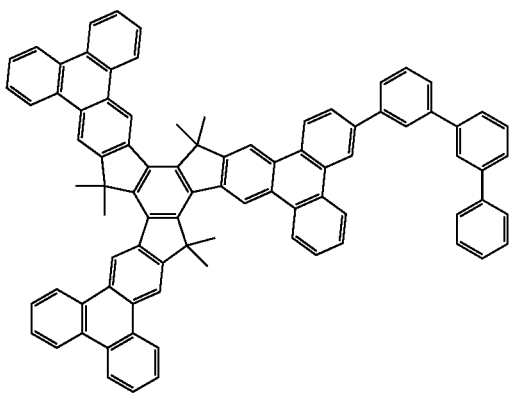

-continued
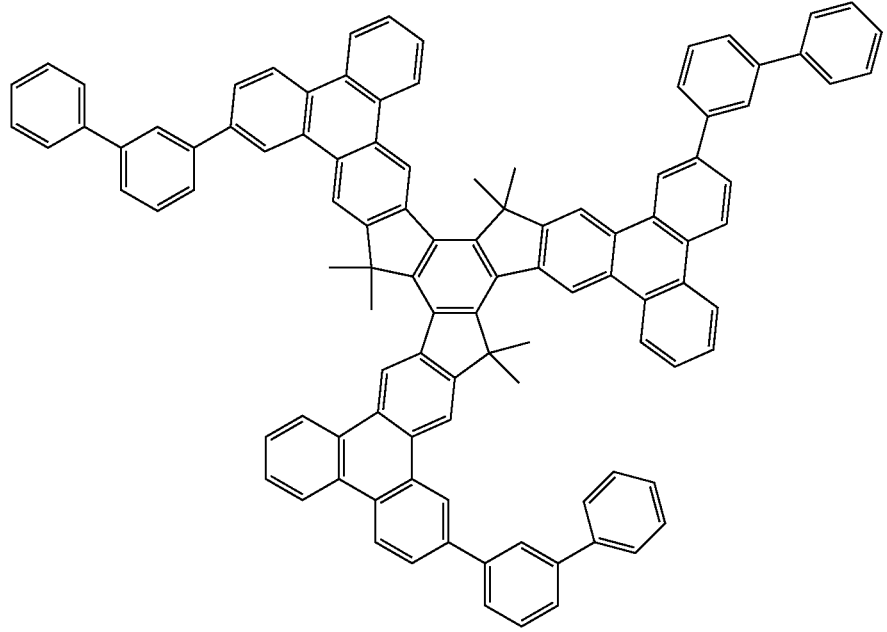
Ex5
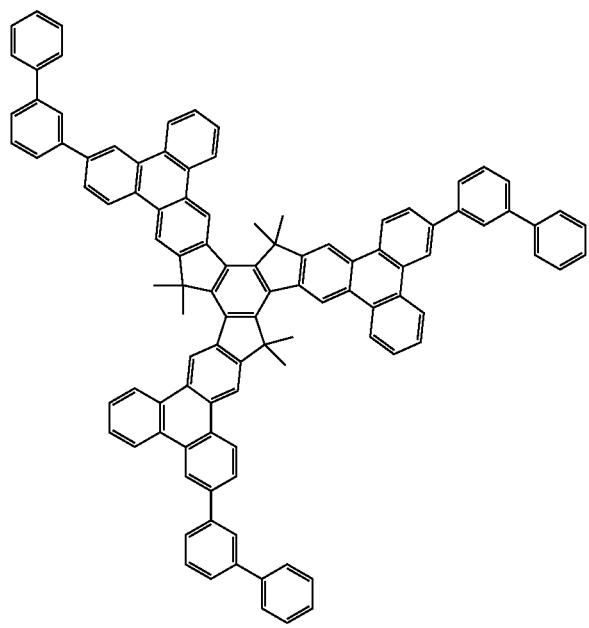
Ex6

-continued
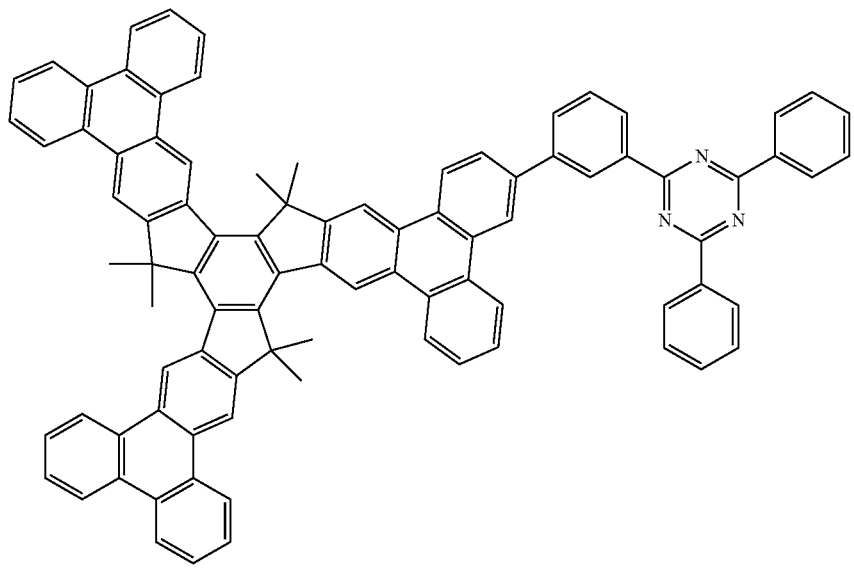
Ex7
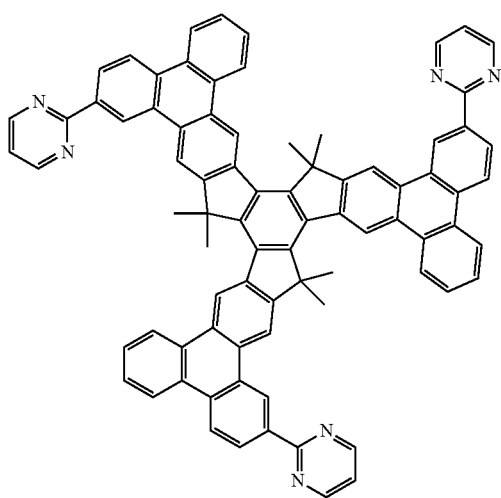
Ex8
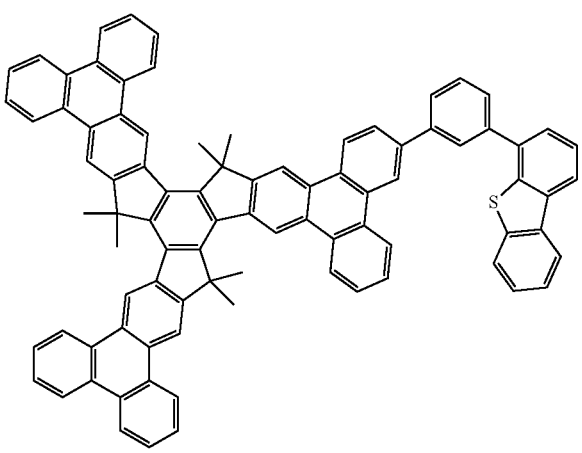
Ex9

-continued
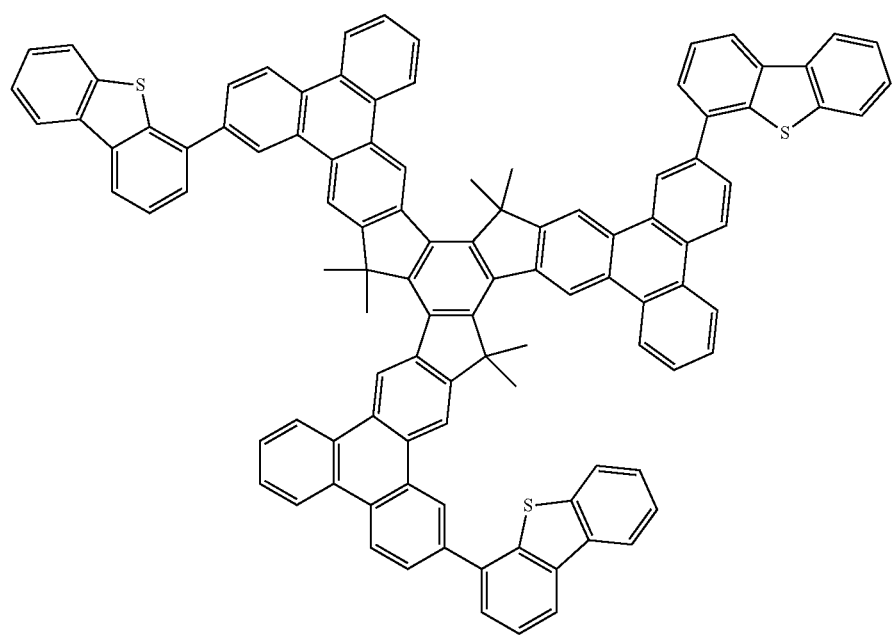
Ex10
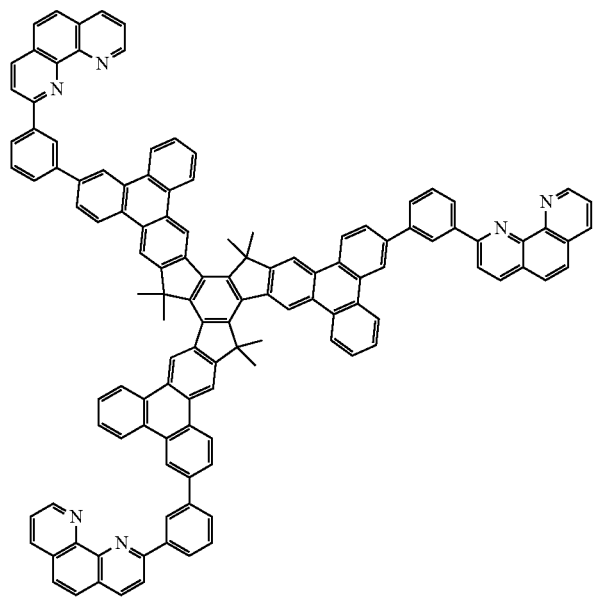
Ex11

Ex12
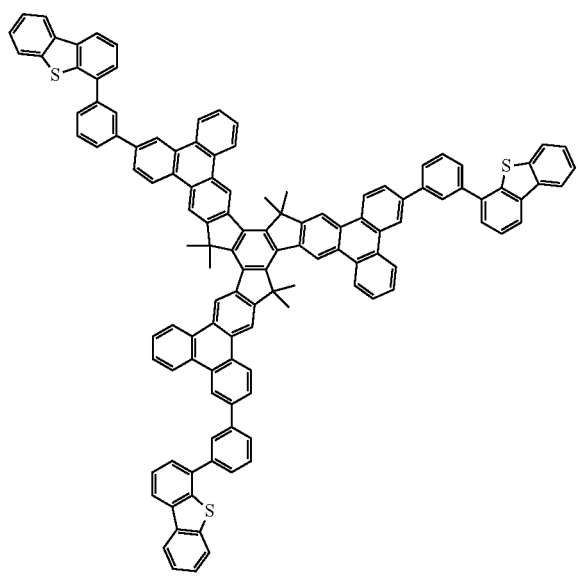
Ex13
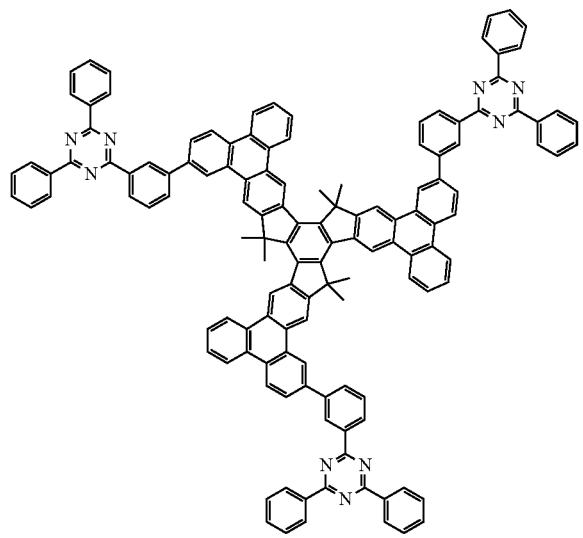
Ex14
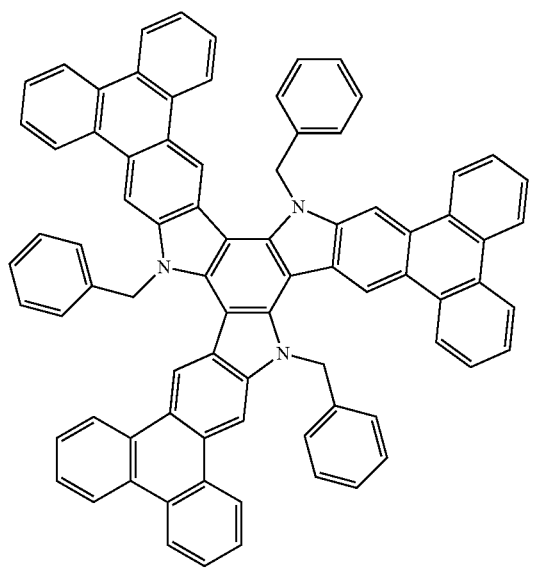
Ex15
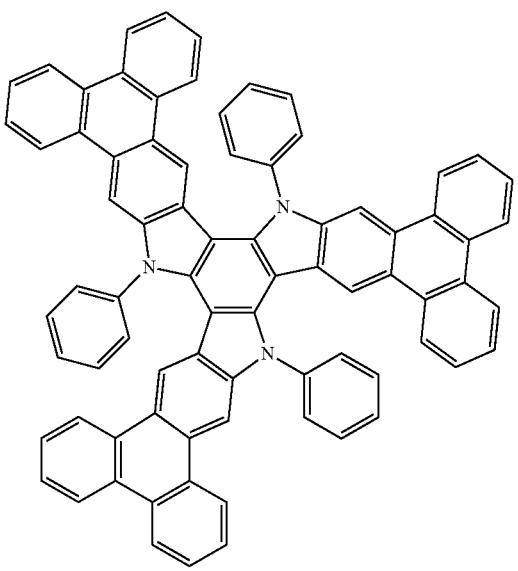

-continued
Ex16
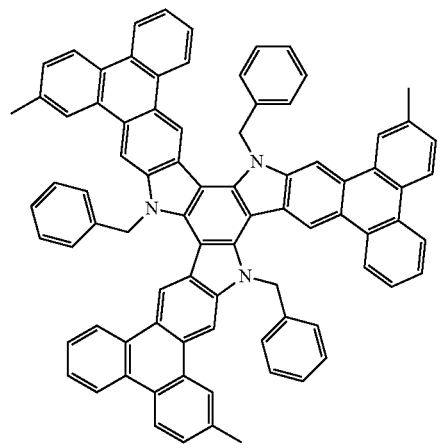
Ex17
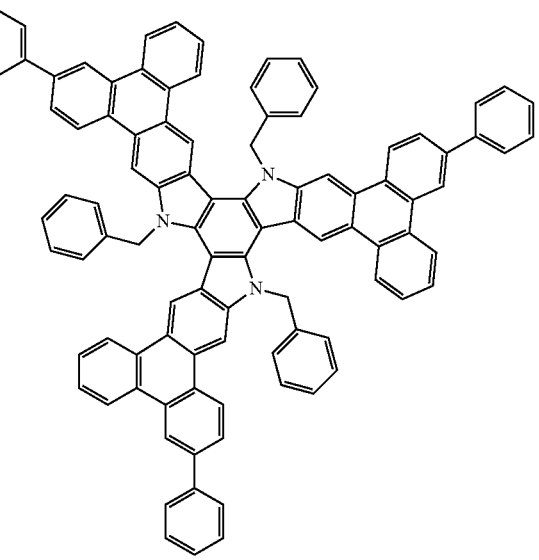
Ex18
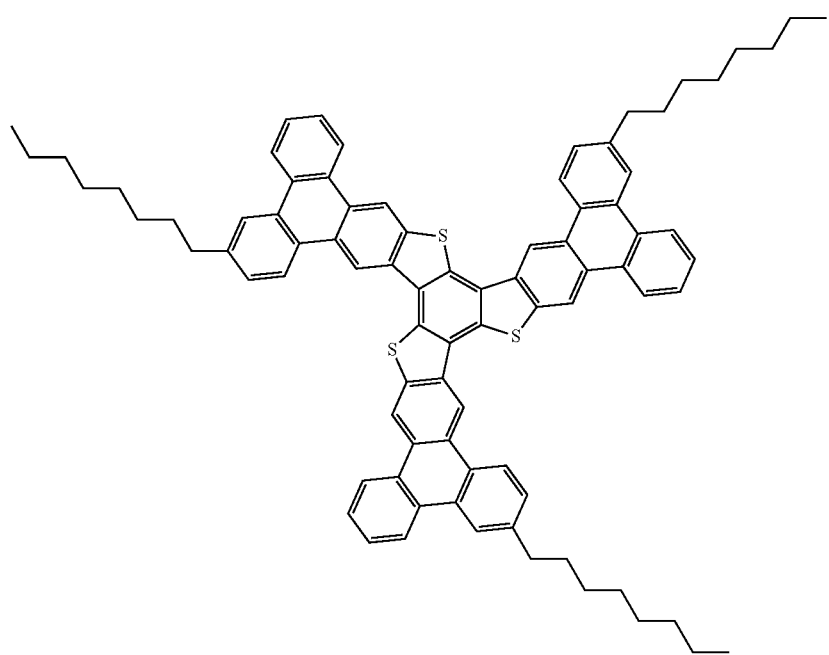

-continued
Ex19
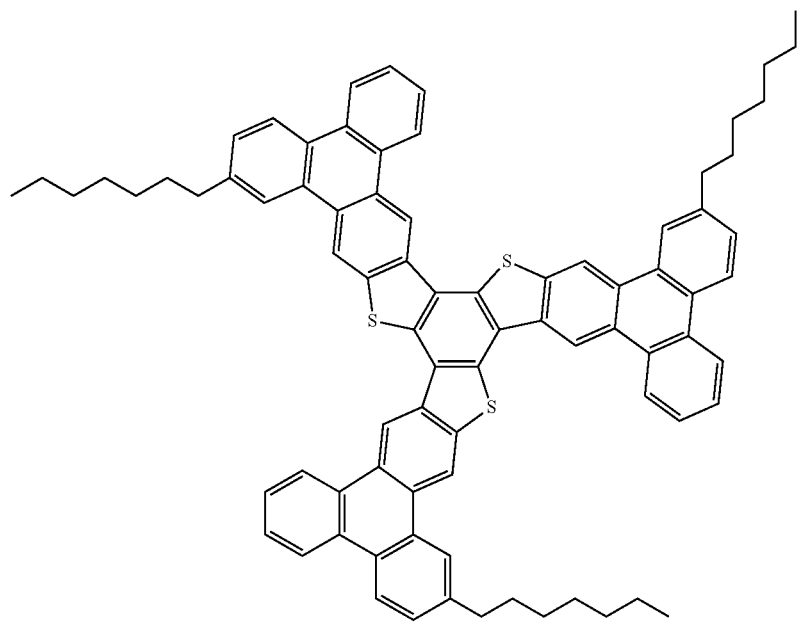
And
Ex20
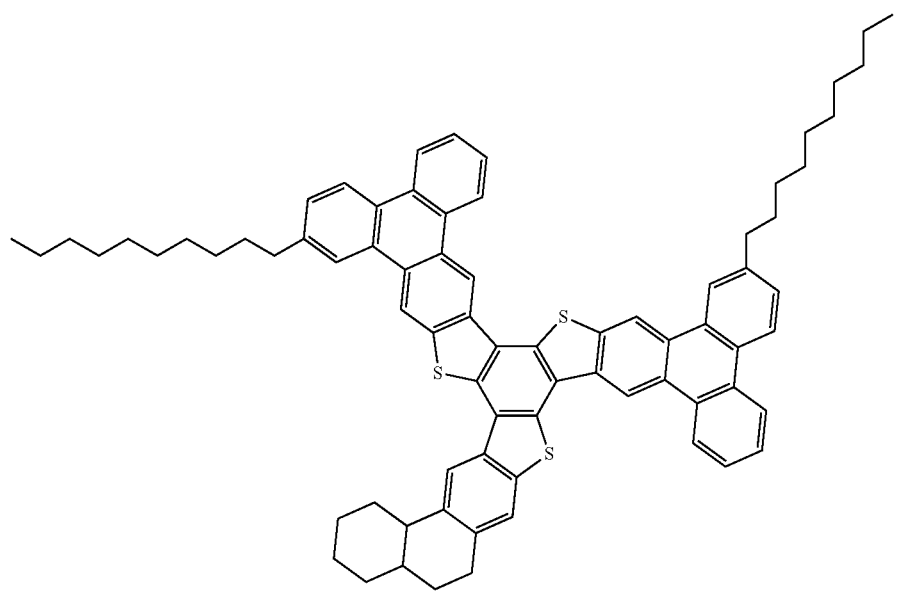
* * * * *